(12) United States Patent
Bhavar et al.

(10) Patent No.: US 9,708,329 B2
(45) Date of Patent: Jul. 18, 2017

(54) SELECTIVE DUAL INHIBITORS OF PI3 DELTA AND GAMMA PROTEIN KINASES

(71) Applicant: Rhizen Pharmaceuticals SA, La Chaux-de-Fonds (CH)

(72) Inventors: Prashant K. Bhavar, Hyderabad (IN); Swaroop K. Vakkalanka, La Chaux-de-Fonds (CH)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

(21) Appl. No.: 14/752,243

(22) Filed: Jun. 26, 2015

(65) Prior Publication Data
US 2015/0376188 A1    Dec. 31, 2015

(30) Foreign Application Priority Data
Jun. 27, 2014   (IN) .......................... 3144/CHE/2014

(51) Int. Cl.
| | | |
|---|---|---|
| *A01N 43/90* | (2006.01) | |
| *A61K 31/519* | (2006.01) | |
| *C07D 487/04* | (2006.01) | |
| *A61K 45/06* | (2006.01) | |
| *C07C 303/38* | (2006.01) | |
| *C07F 5/02* | (2006.01) | |

(52) U.S. Cl.
CPC .......... *C07D 487/04* (2013.01); *A61K 31/519* (2013.01); *A61K 45/06* (2013.01); *C07C 303/38* (2013.01); *C07F 5/025* (2013.01)

(58) Field of Classification Search
CPC .... A61K 31/519; A61K 45/06; C07C 303/38; C07D 487/04; C07F 5/025
See application file for complete search history.

(56) References Cited

U.S. PATENT DOCUMENTS

| | | |
|---|---|---|
| 2011/0118257 A1 | 5/2011 | Muthuppalaniappan et al. |
| 2012/0289496 A1 | 11/2012 | Nagarathnam et al. |

FOREIGN PATENT DOCUMENTS

| | | | |
|---|---|---|---|
| WO | WO-2011055215 A2 | 5/2011 | |
| WO | WO-2012008302 | 1/2012 | |
| WO | WO-2012121953 | 9/2012 | |
| WO | WO 2012151525 A1 * | 11/2012 | ........... C07D 311/22 |
| WO | WO-2012151525 A1 | 11/2012 | |

OTHER PUBLICATIONS

International Search Report dated Sep. 1, 2015 in International Application No. PCT/IB2015/054844.

* cited by examiner

*Primary Examiner* — Jean Cornet
(74) *Attorney, Agent, or Firm* — Blank Rome LLP

(57) ABSTRACT

The present invention relates to a selective dual delta (δ) and gamma (γ) PI3K protein kinase modulator (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl) methane sulfonamide, methods of preparing them, pharmaceutical compositions containing them and methods of treatment, prevention and/or amelioration of PI3K kinase mediated diseases or disorders with them.

10 Claims, 9 Drawing Sheets

SELECTIVE DUAL INHIBITORS OF PI3 DELTA AND GAMMA PROTEIN KINASES

The present application claims the benefit of Indian Patent Application No. 3144/CHE/2014, filed Jun. 27, 2014 which is hereby incorporated by reference in its entirety.

FIELD OF THE INVENTION

The present invention provides dual delta (δ) and gamma (γ) PI3K protein kinase modulators, methods of preparing them, pharmaceutical compositions containing them and methods of treatment, prevention and/or amelioration of PI3K kinase mediated diseases or disorders using them.

BACKGROUND OF THE INVENTION

Phosphoinositide-3 kinase (PI3K) belongs to a class of intracellular lipid kinases that phosphorylate the 3-position hydroxyl group of the inositol ring of phosphoinositide lipids (PIs) generating lipid second messengers. While α and β isoforms of PI3K are ubiquitous in their distribution, expression of δ and γ forms of PI3K is restricted to circulating haematogenous cells and endothelial cells. Unlike PI3Kα or PI3Kβ, mice lacking expression of PI3Kδ or PI3Kγ do not show any adverse phenotype indicating that targeting of these specific isoforms would not result in overt toxicity.

Recently, targeted inhibitors of the PI3K pathway have been suggested as immunomodulatory agents. This interest stems from the fact that the PI3K pathway serves multiple functions in immune cell signaling, primarily through the generation of phosphatidylinositol (3,4,5)-trisphosphate (PIP3), a membrane bound second messenger. PIP3 recruits proteins to the cytoplasmic side of the lipid bilayer, including protein kinases and GTPases, initiating a complex network of downstream signaling cascades important in the regulation of immune cell adhesion, migration, and cell-cell communication.

The four class I PI3K isoforms differ significantly in their tissue distribution. PI3Kα and PI3Kβ are ubiquitous and activated downstream of receptor tyrosine kinases (RTK), whereas PI3Kδ and PI3Kγ are primarily limited to hematopoietic and endothelial cells, and are activated downstream of RTKs, and G protein coupled receptors (GPCR) respectively. Mouse genetic studies have revealed that PI3Kα and PI3Kβ are essential for normal development, whereas loss of PI3Kδ and/or PI3Kγ yields viable offspring with selective immune deficits.

The expression pattern and functions of PI3Kδ and PI3Kγ have generated much interest in developing PI3Kδ/γ inhibitors as active agents for the treatment of many diseases, including, for example, rheumatoid arthritis, allergies, asthma, chronic obstructive pulmonary disease and multiple sclerosis (Hirsch et al., *Pharmacol. Ther.*, 118, 192-205, 2008; Marone et al., *Biochim. Biophys. Acta.*, 1784, 159-185, 2008; Rommel et al., *Nat. Rev. Immunol.*, 7, 191-201, 2007; Ruckle et al., *Nat. Rev. Drug Discov.*, 5, 903-918, 2006). Studies using both pharmacologic and genetic methods have shown these two isoforms often demonstrate synergistic interactions with each other (Konrad et al., *J. Biol. Chem.*, 283, 33296-33303, 2008; Laffargue et al., *Immunity*, 16, 441-451, 2002). In mast cells, for example, PI3Kδ is essential for degranulation in response to IgE cross-linking of Fc-receptors (Ali et al., *J. Immunol.*, 180, 2538-2544, 2008), while PI3Kγ plays an important role in amplifying the response (Laffargue et al., *Immunity*, 16, 441-451, 2002). Similar effects have been seen in other cellular functions, including lymphocyte homing and the neutrophil respiratory burst where PI3Kγ plays a critical role and PI3Kδ amplifies each process. The nonredundant but related roles of PI3Kδ and PI3Kγ have made it difficult to determine which of the two isoforms (alone or in combination) is best targeted in a particular inflammatory disorder.

Studies using mice that lack PI3Kδ and/or PI3Kγ or express kinase-dead variants of PI3Kδ and PI3Kγ have been valuable tools in understanding their roles. For example, PI3Kδ knockout mice demonstrated diminished neutrophil chemotaxis, diminished antibody production (both T cell dependent and independent) (Jou et al., *Mol. Cell. Biol.*, 22, 8580-8591, 2002), and lower numbers of mature B cells (Clayton et al., *J. Exp. Med.*, 196, 753-763, 2002; Jou et al., *Mol. Cell. Biol.*, 22, 8580-8591, 2002), and a decrease in their proliferation in response to anti-IgM (Jou et al., *Mol. Cell. Biol.*, 22, 8580-8591, 2002). This phenotype was replicated in the PI3Kδ kinase-dead variant and with PI3Kδ selective inhibitors along with a decreased number and proliferation of mast cells, and an attenuated allergic response. The PI3Kγ knockout contained higher numbers of, but less responsive, neutrophils, lower numbers of and less responsive macrophages, and dendritic cells displayed decreased mast cell degranulation (Laffargue et al., *Immunity*, 16, 441-451, 2002), a higher ratio of CD4+ to CD8+ T cells, increased thymocyte apoptosis, diminished induction of CXCR3 on activated T cells and decreased cardiac contractility. This latter effect on cardiac tissue was a concern for chronic dosing of patients with PI3Kγ inhibitors. However, this concern was largely mitigated when the PI3Kγ kinase-dead variant (which better mimics inhibition of the kinase rather than loss of the protein) showed similar immune cell phenotypes, but importantly had no cardiac defects. The cardiac effect was later shown to be due to scaffolding effects rather than the catalytic activity of PI3Kγ (Olusegon et al., *Chemistry & Biology*, 1, 123-134, 2010, including the references cited therein). The dual PI3Kδ/PI3Kγ knockout was viable but exhibited serious defects in T cell development and thymocyte survival. The PI3Kγ knockout/PI3Kδ kinase-dead combination produced a similar phenotype suggesting that at least within the immune system, the role of PI3Kδ is likely only a catalytic one. Interpretation of studies using knockout and kinase-dead mice can be challenging because these models provide only a steady-state picture of the immune system, lack temporal and dose control, and do not permit a full understanding of how a dynamic immune response will react to reversible inhibition. Selective inhibitors with varying profiles (PI3Kδ, PI3Kγ, and PI3Kδ/γ) are necessary for studies of leukocyte signaling in order to assess the relative contributions of each PI3K to immune cell activation (Olusegon et al., supra, including the references cited therein).

Dual inhibition of δ/γ is strongly implicated as an intervention strategy in allergic and non-allergic inflammation of the airways and other autoimmune diseases. Scientific evidence for PI3Kδ and PI3Kγ involvement in various cellular processes underlying asthma and chronic obstructive pulmonary disease (COPD) stems from inhibitor studies and gene-targeting approaches (William et. al *Chemistry & Biology*, 17, 123-134, 2010 and Thompson, et al. *Chemistry & Biology*, 17:101-102, 2010). Also, resistance to conventional therapies such as corticosteroids in several COPD patients has been attributed to an up-regulation of the PI3Kδ/γ pathway. Disruption of PI3Kδ/γ signalling therefore provides a novel strategy aimed at counteracting the immuno-inflammatory response. Due to the pivotal role played by PI3Kδ and PI3Kγ in mediating inflammatory cell functionality such as leukocyte migration and activation, and mast cell degranulation, blocking these isoforms may also be an effective strategy for the treatment of rheumatoid arthritis as well. Given the established criticality of these isoforms in immune surveillance, inhibitors specifically targeting the PI3Kδ and PI3Kγ isoforms would be expected to attenuate the progression of immune response encountered in airway inflammation and rheumatoid arthritis (William et. al *Chemistry & Biology*, 17, 123-134, 2010 and Thompson, et al. *Chemistry & Biology*, 17:101-102, 2010)

Reviews and studies regarding PI3K and related protein kinase pathways have been given by Liu et al., *Nature Reviews Drug Discovery*, 8, 627-644, 2009); Nathan et. al., *Mol Cancer Ther.*, 8(1), 2009; Marone et al., *Biochimica et Biophysica Acta*, 1784, 159-185, 2008 and Markman et al., *Annals of Oncology Advance Access*, published August 2009. Similarly reviews and studies regarding role of PI3Kδ and PI3Kγ have been given by William et al., *Chemistry & Biology*, 17, 123-134, 2010 and Timothy et al. *J. Med. Chem.*, 55 (20), 8559-8581, 2012. All of these literature disclosures are hereby incorporated by reference in their entirety.

Compounds such as IPI-145 and CAL130 have been reported as dual inhibitors of Pi3K δ/γ (WO2012/008302 & WO2012/121953 respectively). IPI-145 is under clinical investigation for cancer, asthma and rheumatoid arthritis. IPI-45 has been reported to have a maximum tolerated dose (MTD) of 75 mg BID (55th ASH® Annual Meeting. New Orleans-LA, Dec. 7-10, 2013). There are no reports of CAL-130 being investigated for clinical purposes.

There still remains an unmet need for dual δ/γ PI3K modulators for the treatment of diseases and disorders associated with δ/γ PI3K kinases-mediated events.

Further reference is made herein to International Publication Nos. WO 11/055215 and WO 12/151525 and U.S. Publication Nos. 2011/0118257 and 2012/0289496, each of which is incorporated herein by reference in its entirety.

SUMMARY OF THE INVENTION

The present invention is directed to selective dual inhibitors of PI3K delta (δ) and gamma (γ) protein kinases. These compounds are suitable for use in a pharmaceutical composition for the treatment of PI3K associated diseases, disorders or conditions, e.g., a proliferative disease such as cancer. Inhibition of both PI3Kδ and PI3Kγ protein kinases may provide beneficial effects in the treatment of certain diseases and disorders.

The selective dual inhibitors of the present invention include N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide, pharmaceutically acceptable salts thereof, and prodrugs thereof. For example, the selective dual inhibitor may be selected from the following compounds, pharmaceutically acceptable salts thereof, and prodrugs thereof:

(RS)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide (Compound A); and (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide (Compound A1).

In one embodiment, the compound (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide or a pharmaceutically acceptable salt thereof is substantially free (e.g., contains less than about 10%, such as less than about 5%, less than about 2.5%, less than about 1%, less than about 0.1% by weight) or is free of (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide and pharmaceutically acceptable salts thereof.

In another embodiment, the compound (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide or a pharmaceutically acceptable salt thereof has an enantiomeric excess of greater than about 90%, such as greater than about 91%, greater than about 92%, greater than about 93%, greater than about 94%, greater than about 95%, greater than about 96%, greater than about 97%, greater than about 98%, greater than about 99%, greater than about 99.5%, greater than about 99.9%, or greater than about 99.99%.

In one preferred embodiment, the present invention relates to the compound (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide (Compound A1).

In another embodiment, the present invention relates to the compound (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide or a pharmaceutically acceptable salt thereof.

Another embodiment of the present invention is (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide (Compound A2), a pharmaceutically acceptable salt thereof, or prodrug thereof. Compound A2 is an inhibitor of PI3K delta (δ) protein kinase. These compounds are suitable for use in a pharmaceutical composition for the treatment of PI3K associated diseases, disorders or conditions, e.g., a proliferative disease such as cancer.

The chemical structures of N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide, compound A1, and compound A2 are shown below.

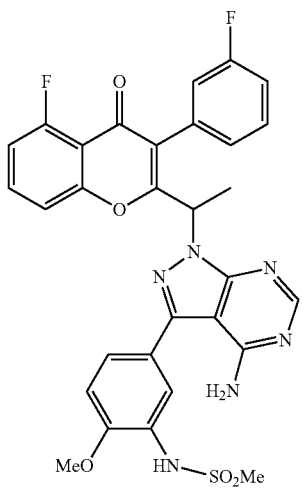 [SMILES: COc1ccc(-c2nn(C(C)c3oc4cccc(F)c4c(=O)c3-c3cccc(F)c3)c3ncnc(N)c23)cc1NS(C)(=O)=O]

-continued (A1)

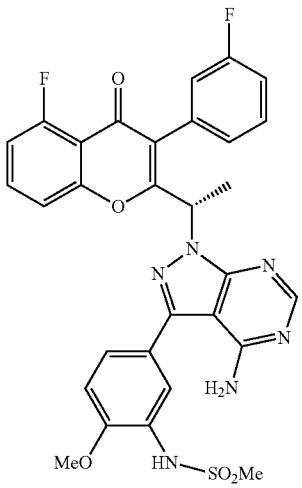

(A2)

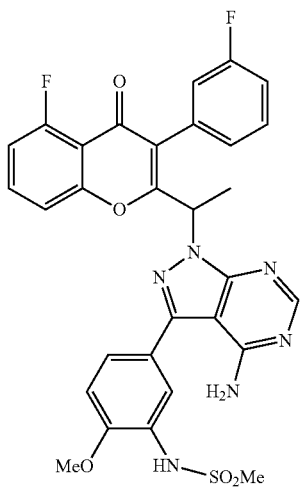

The present invention further provides a pharmaceutical composition comprising one or more compounds of the present invention (such as compound A1) together with a pharmaceutically acceptable carrier. The pharmaceutical composition may further comprise one or more of additional active agents (such as anti-cancer agents and the active agents discussed below). In one embodiment, the pharmaceutical composition includes a therapeutically effective amount of one or more compounds of the present invention.

Another aspect of the present invention relates to a process for the preparation of N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide:

The process comprises the steps of:

(a) reacting 5-bromo-2-methoxyaniline

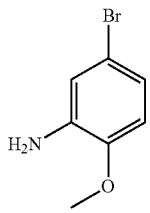

with methane sulphonyl chloride to give N-(5-bromo-2-methoxyphenyl)methanesulfonamide (Intermediate 1):

Intermediate 1

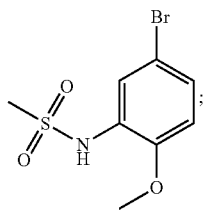

(b) reacting Intermediate 1 with bis(pinacolato)diboron, for example in the presence of potassium acetate, to give N-(2-methoxy-5-(4,4,5,5-tetramethyl-1,3,2-dioxaborolan-2-yl)phenyl)methanesulfonamide (Intermediate 2):

Intermediate 2

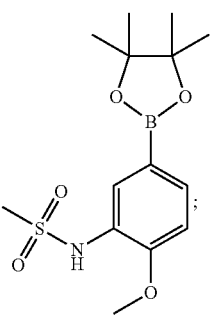

and (c) reacting 2-(1-(4-amino-3-iodo-1H-pyrazolo[3,4-d]pyrimidin-1-yl)ethyl)-5-fluoro-3-(3-fluorophenyl)-4H-chromen-4-one

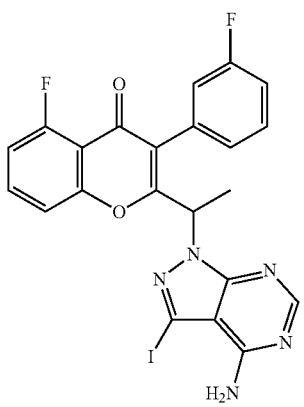 [SMILES: CC(c1oc2cccc(F)c2c(=O)c1-c1cccc(F)c1)n1nc(I)c2c(N)ncnc21]

with intermediate 2 in the presence of a base (such as, for example, sodium carbonate) to give the desired compound N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide;

(d) optionally converting N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide to a pharmaceutically acceptable salt thereof or prodrug thereof.

Yet another embodiment relates to a process for preparation of a compound of formula (A1):

(A1)

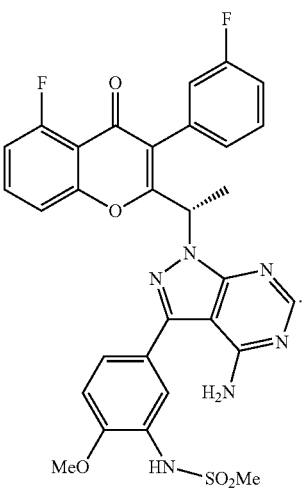

The process comprises the steps of:

(a) subjecting (R)-5-fluoro-3-(3-fluorophenyl)-2-(1-hydroxyethyl)-4H-chromen-4-one:

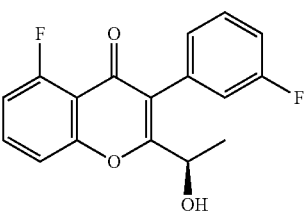 [SMILES: C[C@@H](O)c1oc2cccc(F)c2c(=O)c1-c1cccc(F)c1]

to a Mitsunobu reaction with 3-(4-methoxy-3-nitrophenyl)-1H-pyrazolo[3,4-d]pyrimidin-4-amine:

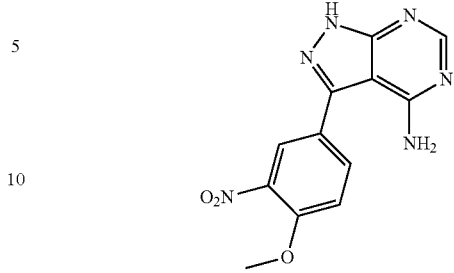

(for example, in the presence of triphenylphosphine and diisopropylazodicarboxylate) to give (S)-2-(1-(4-amino-3-(4-methoxy-3-nitrophenyl)-1H-pyrazolo[3,4-d]pyrimidin-1-yl)ethyl)-5-fluoro-3-(3-fluorophenyl)-4H-chromen-4-one (Intermediate 3):

Intermediate 3

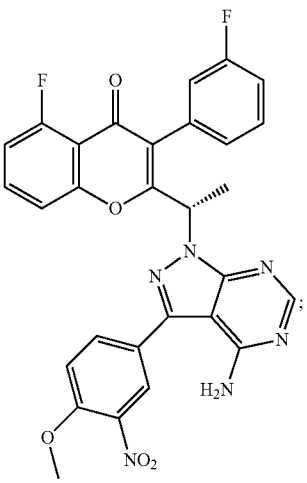

(b) reducing Intermediate 3, for example with a reducing agent such as Raney Ni, to give (S)-2-(1-(4-amino-3-(3-amino-4-methoxyphenyl)-1H-pyrazolo[3,4-d]pyrimidin-1-yl)ethyl)-5-fluoro-3-(3-fluorophenyl)-4H-chromen-4-one (Intermediate 4):

Intermediate 4

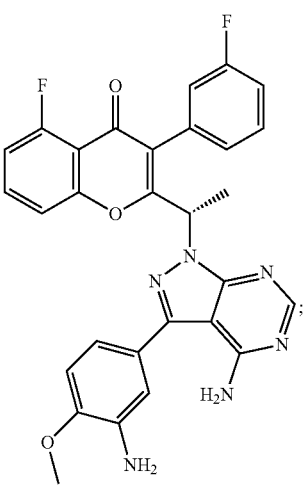

(c) treating Intermediate 4 with methanesulphonyl chloride to give the desired compound of the formula (A1); and (d) optionally converting compound (A1) to a pharmaceutically acceptable salt thereof or prodrug thereof.

Yet another embodiment are intermediates useful for preparing the compounds of the present invention such as (S)-2-(1-(4-amino-3-(4-methoxy-3-nitrophenyl)-1H-pyrazolo[3,4-d]pyrimidin-1-yl)ethyl)-5-fluoro-3-(3-fluorophenyl)-4H-chromen-4-one, (S)-2-(1-(4-amino-3-(3-amino-4-methoxyphenyl)-1H-pyrazolo[3,4-d]pyrimidin-1-yl)ethyl)-5-fluoro-3-(3-fluorophenyl)-4H-chromen-4-one, and salts thereof.

Yet another embodiment of the present invention is a method of inhibiting PI3Kδ and PI3Kγ in a patient comprising administering to the patient an effective amount of at least one compound of the present invention.

Yet another embodiment of the present invention is a method of inhibiting PI3Kδ in a patient comprising administering to the patient an effective amount of at least one of (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide (compound A2), a pharmaceutically acceptable salt thereof, or a prodrug thereof.

Yet another embodiment of the present invention is a method of treating, preventing, and/or inhibiting a PI3K protein kinase mediated disease, disorder or condition (such a proliferative disease or disorder, e.g., cancer) in a patient comprising administering to the patient an effective amount of at least one compound of the present invention.

Yet another embodiment of the present invention is a method for inhibiting PI3K, in particular PI3Kδ and PI3Kγ, in a patient comprising administering to the patient an effective amount of at least one compound of the present invention.

Yet another embodiment of the present invention is a method for treating an inflammatory, autoimmune or proliferative disease via modulation of a protein kinase (such as PI3Kδ and PI3Kγ) comprising administering to a patient in need of such treatment an effective amount of at least one compound of the present invention. In one embodiment, the compound of the present invention inhibits both PI3Kδ and PI3Kγ.

Yet another embodiment of the present invention is a method for treating an inflammatory, autoimmune or proliferative disease via modulation of a protein kinase (such as PI3Kδ and PI3Kγ) by administering to a patient in need of such treatment an effective amount of at least one compound of the present invention, in combination (simultaneously or sequentially) with at least one other anti-inflammatory, immunomodulator or anti-cancer agent, or a combination thereof. In one embodiment, the compound of the present invention inhibits both PI3Kδ and PI3Kγ.

The compounds of the present invention are useful in the treatment of a variety of cancers, including, but not limited to:

carcinoma, including, but not limited to, that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkett's lymphoma;

hematopoietic tumors of myeloid lineage, including, but not limited to, acute and chronic myelogenous leukemias, myelodysplastic syndrome and promyelocytic leukemia;

tumors of mesenchymal origin, including, but not limited to, fibrosarcoma and rhabdomyosarcoma;

tumors of the central and peripheral nervous system, including, but not limited to, astrocytoma, neuroblastoma, glioma and schwannomas; and other tumors, including, but not limited to, melanoma, seminoma, teratocarcinoma, osteosarcoma, xenoderoma pigmentosum, keratoctanthoma, thyroid follicular cancer and Kaposi's sarcoma.

In one embodiment, an effective amount of a compound of the present invention is administered to treat a leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, Burkett's lymphoma, acute and chronic myelogenous leukemias, myelodysplastic syndrome or promyelocytic leukemia.

Due to the key role of protein kinases in the regulation of cellular proliferation in general, the compounds of the present invention may act as reversible cytostatic agents, and may therefore be useful in the treatment of any disease process which features abnormal cellular proliferation, such as, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including, but not limited to, those types mentioned herein above), viral infections (including, but not limited to, herpes virus, poxvirus, Epstein-Barr virus, Sindbis virus and adenovirus), autoimmune diseases (including, but not limited to, systemic lupus, erythematosus, autoimmune mediated glomerulonephritis, rheumatoid arthritis, psoriasis, inflammatory bowel disease, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, haematological diseases (including, but not limited to, chronic anemia and aplastic anemia), degenerative diseases of the musculoskeletal system (including, but not limited to, osteoporosis and arthritis) aspirin-sensitive rhinosinusitis, cystic fibrosis, multiple sclerosis, kidney diseases and cancer pain. The compounds of the present invention are also useful in the prevention, inhibition, or suppression of AIDS development in HIV-infected individuals.

The compounds of the present invention may modulate the level of cellular RNA and DNA synthesis. The compounds of the present invention are therefore useful in the treatment of viral infections, including, but not limited to, HIV, human papilloma virus, herpes virus, poxvirus, Epstein-Barr virus, Sindbis virus and adenovirus.

The compounds of the present invention are useful in the chemoprevention of cancer. Chemoprevention is defined herein as inhibiting the development of invasive cancer by either blocking the initiating mutagenic event or by blocking the progression of pre-malignant cells that have already suffered an insult or inhibiting tumor relapse. The compounds of the present invention are also useful in inhibiting tumor angiogenesis and metastasis. One embodiment of the present invention is a method of inhibiting tumor angiogenesis or metastasis in a patient in need thereof by administering an effective amount of one or more compounds of the present invention.

Another embodiment of the present invention is a method of treating an immune system-related disease or immune disorder (e.g., an autoimmune disease), a disease or disorder involving inflammation (e.g., asthma, chronic obstructive pulmonary disease (COPD), rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder. The method includes administering an effective amount of one or more compounds of the present invention.

Examples of immune disorders include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune haemolytic anemia, multiple sclerosis, cystic fibrosis, chronic relapsing hepatitis, primary biliary cirrhosis, allergic conjunctivitis and atopic dermatitis.

In one embodiment, the compounds described herein are useful as immunosuppresants to prevent transplant graft rejections, allogeneic or xenogeneic transplantation rejection (organ, bone marrow, stem cells, other cells and tissues), and graft—versus—host disease. In one particular embodiment, transplant graft rejections result from tissue or organ transplants. In further embodiments, the graft-versus-host disease results from bone marrow or stem cell transplantation. One embodiment of the present invention is a method of preventing or decreasing the risk of transplant graft rejection, allogeneic or xenogeneic transplantation rejection (organ, bone marrow, stem cells, other cells and tissues) or graft—versus—host disease comprising administering an effective amount of one or more compounds of the present invention.

The compounds of the present invention are also useful in combination (administered together or sequentially) with known anti-cancer treatments, such as, for example, radiation therapy or with cytostatic or cytotoxic or anticancer agents, such as, for example, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors, such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); BTK inhibitor, such as ibrutinib; and other protein kinase modulators, and any combination thereof.

The compounds of the present invention are also useful in combination (administered together or sequentially) with one or more steroidal anti-inflammatory drugs, non-steroidal anti-inflammatory drugs (NSAIDs) and immune selective anti-inflammatory derivatives (ImSAIDs), and any combination thereof.

The present invention further provides a pharmaceutical composition comprising one or more compounds of the present invention and a pharmaceutically acceptable carrier. The pharmaceutical composition may further comprise one or more of the active ingredients identified above, such as other anti-cancer agents.

Yet another embodiment is a method of treating leukemia in a patient in need thereof comprising administering a therapeutically effective amount of a compound of the present invention. In one embodiment, the leukemia is selected from chronic lymphocytic leukemia (CLL), non-Hodgkin lymphoma (NHL), Hodgkin lymphoma (HL), acute myeloid leukemia (AML), multiple myeloma (MM), small lymphocytic lymphoma (SLL), and indolent non-Hodgkin's lymphoma (I-NHL).

Yet another embodiment of the present invention is a method of treating an autoimmune disorder in a patient in need thereof comprising administering a therapeutically effective amount of a compound of the present invention. In one embodiment, the autoimmune disorder is selected from asthma, COPD, rheumatoid arthritis, psoriasis, lupus and experimental autoimmune encephalomyelitis (EAE).

Yet another embodiment of the present invention is a method of treating allergic rhinitis in a patient in need thereof comprising administering to the patient a therapeutically effective amount of a compound of the present invention.

In any of the aforementioned methods, the compound(s) of the present invention and optional additional active agents can be administered in the form of a pharmaceutical composition as described herein.

DETAILED DESCRIPTION OF THE INVENTION

Figure 1:
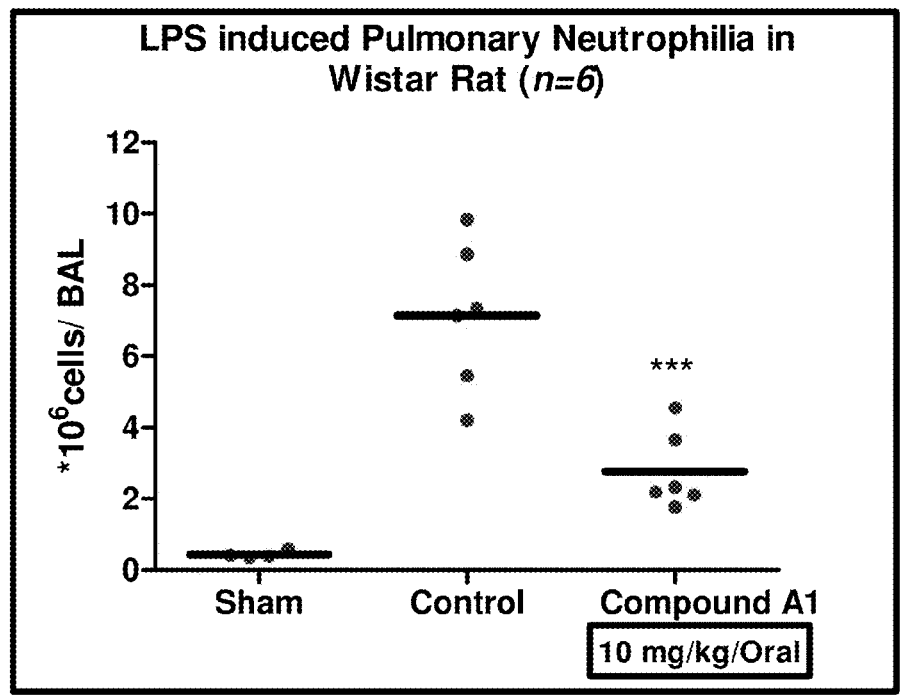
FIG. 1 depicts a bar graph of the neutrophil count in bronchoalveolar lavage fluid (BALF) from female Wistar rats treated with 10 mg/kg of Compound A1 (po) according to the lipopolysaccharide induced pulmonary neutrophilia model described in Assay 7.

As used herein the following definitions shall apply unless otherwise indicated. Further many of the groups defined herein can be optionally substituted. The listing of substituents in the definition is exemplary and is not to be construed to limit the substituents defined elsewhere in the specification.

Certain of the compounds described herein contain one or more asymmetric centers and can thus give rise to enantiomers, diastereomers, and other stereoisomeric forms that can be defined, in terms of absolute stereochemistry, as (R)- or (S)-. Unless otherwise specified, the present chemical entities, pharmaceutical compositions and methods are meant to include all such possible isomers, including racemic mixtures, optically pure forms and intermediate mixtures. For the instance, non-limiting example of intermediate mixtures include a mixture of R:S or S:R isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The term "prodrug" refers to a compound, which is an inactive precursor of a compound that is converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulphate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR' (where R is a drug and R' is a chemical group).

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which may be sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; AIDS=Acquired Immuno Deficiency Syndrome; HIV=Human Immunodeficiency Virus; MeI=Methyl Iodide; ND: Not determined.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but, not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal (e.g., a dog, cat, horse, or pig), such as a mammal, for example a human. The methods described herein can be useful in both human therapeutics and veterinary applications. In some embodiments, the patient is a mammal. In a preferred embodiment, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including, without limitation, x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signalling molecule.

The term "selective inhibition" or "selectively inhibit" as applied to a biologically active agent refers to the agent's ability to selectively reduce the target signalling activity as compared to off-target signalling activity, via direct or indirect interaction with the target.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavouring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

In other embodiments, the compounds of the present invention selectively inhibit one or more members of type I or class I phosphatidylinositol 3-kinases (PI3-kinase) with an $IC_{50}$ value of about 100 nM or less, about 50 nM or less, about 10 nM or less, about 5 nM or less, about 100 μM or less, about 10 μM or less, or about 1 μM or less as measured in an in vitro kinase assay.

In yet another aspect, an inhibitor that selectively inhibits one or more members of type I PI3-kinases, or an inhibitor that selectively inhibits one or more type I PI3-kinase mediated signalling pathways, alternatively can be understood to refer to a compound that exhibits a 50% inhibitory concentration ($IC_{50}$) with respect to a given type I PI3-kinase, that is at least 10-fold lower, at least 20-fold lower, at least 50-fold lower, at least 100-fold lower, or at least 1000-fold lower than the inhibitor's $IC_{50}$ with respect to the rest of the other type I PI3-kinases.

As used herein, the term "dual PI3-kinase δ/γ inhibitor" and "dual PI3-kinase δ/γ selective inhibitor" refers to a compound that inhibits the activity of both the PI3-kinase δ and γ isozyme more effectively than other isozymes of the PI3K family. A dual PI3-kinase δ/γ inhibitor is therefore more selective for PI3-kinase δ and γ than conventional PI3K inhibitors such as CAL-130, wortmannin and LY294002, which are nonselective PI3K inhibitors.

Inhibition of PI3-kinase δ and γ may be of therapeutic benefit in treatment of various conditions, e.g., conditions characterized by an inflammatory response including, but not limited to, autoimmune diseases, allergic diseases, and arthritic diseases. Importantly, inhibition of PI3-kinase δ and γ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defence system as well as conditions associated with reactions of the non-specific defence system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia).

"Allergic disease" as used herein refers to any symptoms, tissue damage, or loss of tissue function resulting from allergy.

"Arthritic disease" as used herein refers to any disease that is characterized by inflammatory lesions of the joints attributable to a variety of etiologies.

"Dermatitis" as used herein refers to any of a large family of diseases of the skin that are characterized by inflammation of the skin attributable to a variety of etiologies.

As previously described, the term "dual PI3-kinase δ/γ selective inhibitor" generally refers to a compound that inhibits the activity of the PI3-kinase δ and γ isozyme more effectively than other isozymes of the PI3K family. The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a dual PI3-kinase δ/γ selective inhibitor alternatively can be understood to refer to a compound that exhibits a 50% inhibitory concentration ($IC_{50}$) with respect to PI3-kinase δ and γ, that is at least 10-fold lower, at least 20-fold lower, or at least 30-fold lower than the $IC_{50}$ value with respect to any or all of the other class I PI3K family members. In an alternative embodiment of the invention, the term dual PI3-kinase δ/γ selective inhibitor can be understood to refer to a compound that exhibits an $IC_{50}$ with respect to PI3-kinase δ and γ that is at least 30-fold lower, at least 50-fold lower, at least 100-fold lower, at least 200-fold lower, or at least 500-fold lower than the $IC_{50}$ with respect to any or all of the other PI3K class I family members. A dual PI3-kinase δ/γ selective inhibitor is typically administered in an amount such that it selectively inhibits both PI3-kinase δ and γ activity, as described above.

In certain embodiments, the compounds of the present invention exhibit PI3-kinase δ and γ inhibition almost equally (~1:1) or at a maximum ratio of 1:5, i.e., the compound the of the present invention exhibit almost equal $IC_{50}$ values for both PI3-kinase δ and γ enzyme, or at most a 3 to 8 fold difference between the two.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "in vitro" means outside of a living individual. Examples of ex vivo cell populations include in vitro cell cultures and biological samples including but not limited to fluid or tissue samples obtained from individuals. Such samples may be obtained by methods known in the art.

Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PI3-kinase δ selective inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

The compounds of the present invention can be prepared by methods known in the art, such as those described in International Publication Nos. WO 2011/055215, WO 2012/151525, and WO 2013/164801, each of which is hereby incorporated by reference in its entirety.

Pharmaceutical Compositions

The present invention also provides a pharmaceutical composition comprising one or more compounds of the present invention and one or more pharmaceutically acceptable carriers or excipients. In one embodiment, the pharmaceutical composition includes a therapeutically effective amount of one or more compounds of the present invention. The pharmaceutical composition may include one or more additional active ingredients as described herein.

The pharmaceutical carriers and/or excipients may be selected from, for example, diluents, fillers, salts, disintegrants, binders, lubricants, glidants, wetting agents, controlled release matrices, colorants, flavourings, buffers, stabilizers, solubilizers, and combinations thereof.

In one embodiment, the pharmaceutical compositions described herein contain from about 0.1 mg to about 1,000 mg, such as from about 1 mg to about 1,000 mg, from about 20 mg to about 800 mg, from about 50 mg to about 600 mg or from about 50 mg to about 600 mg of one or more compounds of the present invention. In another embodiment, the pharmaceutical compositions described herein contain from about 100 mg to about 400 mg of one or more compounds of the present invention.

The pharmaceutical compositions of the present invention can be administered alone or in combination with one or more other active agents. Where desired, the subject compounds and other agent(s) may be mixed into a preparation or both components may be formulated into separate preparations to use them in combination separately or at the same time.

The compounds and pharmaceutical compositions of the present invention can be administered by any route that enables delivery of the compounds to the site of action, such as orally, intranasally, topically (e.g., transdermally), intraduodenally, parenterally (including intravenously, intraarterially, intramuscularally, intravascularally, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea).

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

Methods of Treatment

The amount of the compound to be administered is dependent on the mammal being treated, the severity of the disorder or condition, the rate of administration, the disposition of the compound and the discretion of the prescribing physician. However, an effective dosage is in the range of from about 0.001 to about 100 mg/kg body weight per day, preferably from about 1 to about 35 mg/kg/day, in single or divided doses. For a 70 kg human, this would amount to from about 0.05 to about 7 g/day, preferably from about 0.05 to about 2.5 g/day An effective amount of a compound of the invention may be administered in either single or multiple doses (e.g., twice or three times a day).

The compounds of the present invention may be used in combination with one or more of anti-cancer agents (e.g., chemotherapeutic agents), therapeutic antibodies, and radiation treatment.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs).

EXAMPLES

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The intermediates described herein may be prepared by the methods described in International Publication Nos. WO 11/055215 and WO 12/151525, both of which are hereby incorporated by reference.

Intermediate 1:
N-(5-bromo-2-methoxyphenyl)methanesulfonamide

To a solution of 5-bromo-2-methoxyaniline (1.00 g, 4.94 mmol) in dichloromethane (10 ml), pyridine (0.800 ml, 9.89 mmol) was added and cooled to 0° C. Methane sulphonyl chloride (0.40 ml, 5.19 mmol) was added and stirred for 30 min. The reaction mixture was quenched with water, extracted with ethyl acetate, dried over anhydrous sodium sulphate and concentrated under reduced pressure. The crude product was chromatographed with ethyl acetate: petroleum ether to afford the title compound as a reddish solid (1.20 g, 87%).

Intermediate 2: N-(2-methoxy-5-(4,4,5,5-tetramethyl-1,3,2-dioxaborolan-2-yl)phenyl)methanesulfonamide Potassium acetate (0.841 g, 8.57 mmol) and bis(pinacolato)diboron (1.190 g, 4.71 mmol) were added to a solution of intermediate 1 (1.20 g, 4.28 mmol) in dioxane (17.5 ml) and the solution was degassed for 30 min. [1,1'-Bis(diphenylphosphino)ferrocene]dichloro palladium(II). CH$_2$Cl$_2$ (0.104 g, 0.128 mmol) was added under nitrogen atmosphere and heated to 80° C. After 2 h the reaction mixture was filtered through celite and concentrated. The crude product was purified by column chromatography with ethyl acetate:petroleum ether to afford the title compound as a yellow solid (1.00 g, 71%). $^1$H-NMR (δ ppm, CDCl$_3$, 400 MHz): 7.91 (d, J=1.2 Hz, 1H), 7.62 (dd, J=8.1, 1.2 Hz, 1H), 6.92 (d, J=8.1 Hz, 1H), 6.73 (s, 1H), 3.91 (s, 3H), 2.98 (s, 3H), 1.32 (s, 12H).

Intermediate 3: (S)-2-(1-(4-amino-3-(4-methoxy-3-nitrophenyl)-1H-pyrazolo[3,4-d]pyrimidin-1-yl)ethyl)-5-fluoro-3-(3-fluorophenyl)-4H-chromen-4-one (S)-2-(1-(4-amino-3-(4-methoxy-3-nitrophenyl)-1H-pyrazolo[3,4-d]pyrimidin-1-yl)ethyl)-5-fluoro-3-(3-fluorophenyl)-4H-chromen-4-one: To a solution of (R)-5-fluoro-3-(3-fluorophenyl)-2-(1-hydroxyethyl)-4H-chromen-4-one (0.500 g, 1.64 mmol) in THF (5 ml), 3-(4-methoxy-3-nitrophenyl)-1H-pyrazolo[3,4-d]pyrimidin-4-amine (0.564 g, 1.97 mmol) and triphenylphosphine (0.649 g, 2.47 mmol) were added followed by the addition of diisopropylazodicarboxylate (0.50 ml, 2.47 mmol). ((R)-5-fluoro-3-(3-fluorophenyl)-2-(1-hydroxyethyl)-4H-chromen-4-one can be prepared as described for Intermediates 23, 25, and 26 in International Publication No. WO 2012/151525). After 4 h at room temperature, the mixture was concentrated and the residue was purified by column chromatography with ethyl acetate:petroleum ether to afford the title compound as a brown solid (0.270 g, 29%). $^1$H-NMR (δ ppm, DMSO-d6, 400 MHz): 8.04 (s, 1H), 7.83 (m, 1H), 7.63-7.50 (m, 3H), 7.29 (m, 2H), 7.06 (dt, J=8.7, 2.2 Hz, 1H), 6.94 (m, 2H), 6.75 (dd, J=8.1, 2.1 Hz, 1H), 5.95 (q, J=7.0 Hz, 1H), 4.98 (s, 2H), 3.81 (s, 3H), 1.86 (d, J=7.0 Hz, 3H).

Intermediate 4: (S)-2-(1-(4-amino-3-(3-amino-4-methoxyphenyl)-1H-pyrazolo[3,4-d]pyrimidin-1-yl)ethyl)-5-fluoro-3-(3-fluorophenyl)-4H-chromen-4-one (S)-2-(1-(4-amino-3-(3-amino-4-methoxyphenyl)-1H-pyrazolo[3,4-d]pyrimidin-1-yl)ethyl)-5-fluoro-3-(3-fluorophenyl)-4H-chromen-4-one: To a solution of Intermediate 3 (0.260 g, 0.455 mmol) in ethanol (5 ml), Raney Ni (0.130 g) was added and hydrogeneated at 20 psi at 50° C. for 24 h. The reaction mixture was passed through celitepad and concentrated to afford the title compound as a brown solid (0.150 g, 60%). Mass: 540.8 (M+).

Example A

N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide To a solution of 2-(1-(4-amino-3-iodo-1H-pyrazolo[3,4-d]pyrimidin-1-yl)ethyl)-5-fluoro-3-(3-fluorophenyl)-4H-chromen-4-one (0.200 g, 0.366 mmol) in DME (2.1 ml) and water (0.67 ml), intermediate 2 (0.179 g, 0.550 mmol) and sodium carbonate (0.116 g, 1.10 mmol) were added and the system was degassed for 30 min. (2-(1-(4-amino-3-iodo-1H-pyrazolo[3,4-d]pyrimidin-1-yl)ethyl)-5-fluoro-3-(3-fluorophenyl)-4H-chromen-4-one can be prepared as described for Intermediates 23, 25, and 26 in International Publication No. WO 2012/151525). Bis(diphenylphosphino) ferrocene]dichloropalladium(II) (0.059 g, 0.075 mmol) was added and kept under microwave irradiation (microwave power=100 W, temperature=100° C.) for 45 min. The reaction mixture was Celite filtered, concentrated and extracted with ethyl acetate. The organic layer was dried over sodium sulphate and concentrated under reduced pressure. The crude product was purified by column chromatography with methanol:dichloromethane to afford the title compound as a brown solid (0.080 g, 35%). MP: 216-218° C. $^1$H-NMR (δ ppm, CDCl$_3$, 400 MHz): 8.20 (s, 1H), 7.73 (s, 1H), 7.53 (m, 2H), 7.31 (m, 2H), 7.07-6.73 (m, 6H), 6.07 (q, J=6.2 Hz, 1H), 3.98 (s, 3H), 3.14 (s, 3H), 2.01 (d, J=6.0 Hz, 3H).

Example A1 and A2

Method A (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide and (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide

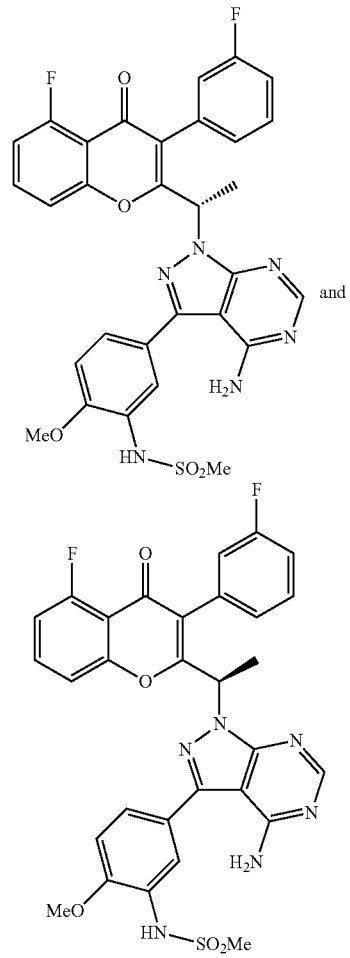

The two enantiomerically pure isomers were separated by preparative SFC (supercritical fluid) conditions from N-(5-

(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide (0.500 g) on a CHIRALPAK AS-H column (250×30 mm; 5 μm) using methanol:$CO_2$ (55:45) as the mobile phase at a flow rate of 80 g/min.

Example A1 (S-isomer): Brown solid (0.247 g). Enantiomeric excess: 97.4%. Retention time: 2.14 min. Mass: 619.1 (M++1). MP: 156-158° C.

Example A2 (R-isomer): Brown solid (0.182 g). Enantiomeric excess: 99.3%. Retention t: 3.43 min. Mass: 619.1 (M++1). MP: 168-171° C.

Method A1

(S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide and (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide

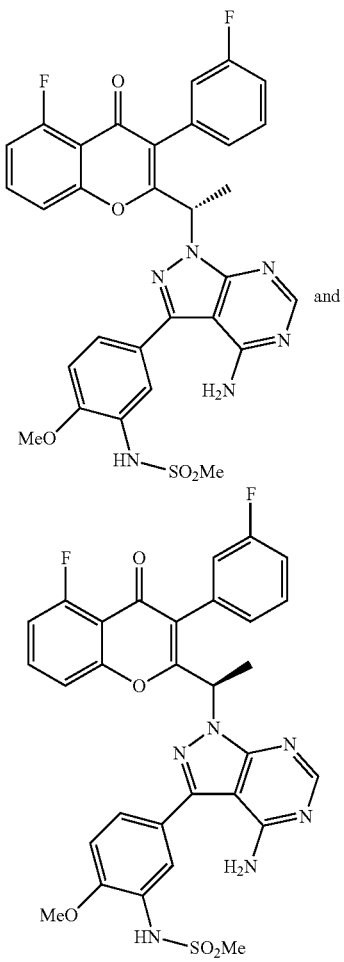

The two enantiomerically pure isomers were separated by preparative SFC (supercritical fluid) conditions from N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl) methanesulfonamide (15.0 g) on a CHIRALPAK AS-H column (250×20 mm; 5 μm) using methanol:$CO_2$ (45:55) as the mobile phase at a flow rate of 120 g/min.

Example A1 (S-isomer): Enantiomeric excess: 100%. Retention time: 2.21 min. Mass: 619.1 (M++1). MP: 175-178° C. Specific optical rotation (C=1 in chloroform, at 25° C.): $[\alpha]_D$=+147.16.

Example A2 (R-isomer): Enantiomeric excess: 99.3%. Retention t: 3.72 min. Mass: 619.1 (M++1). MP: 154-157° C. Specific optical rotation (C=1 in chloroform, at 25° C.): $[\alpha]_D$=−159.54.

Method B

Example A1

(S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide To a solution of Intermediate 4 (0.500 g, 0.923 mmol) in dichloromethane (5 ml) cooled to 0° C., pyridine (0.200 ml, 1.84 mmol) was added and stirred for 10 min. Methanesulphonyl chloride (0.100 ml, 0.923 mmol) was added stirred for 30 min. The reaction mixture was quenched with water, extracted with dichloromethane and dried over sodium sulphate. The crude product was column chromatographed with methanol:dichloromethane to afford the title compound as an off-white solid (0.240 g, 42%). MP: 211-213° C. $^1$H-NMR (δ ppm, DMSO-d6, 400 MHz): 9.15 (s, 1H), 8.06 (s, 1H), 7.83 (m, 1H), 7.49 (m, 4H), 7.28 (m, 4H), 7.08 (dt, J=8.6, 1.7 Hz, 1H), 6.92 (s, 2H), 5.98 (q, J=6.9 Hz, 1H), 3.88 (s, 3H), 2.99 (s, 3H), 1.88 (d, J=7.0 Hz, 3H). Enantiomeric excess: 85.4% as determined by HPLC on a chiralpak AS-3R column, enriched in the fast eluting isomer (retention time=7.46 min.).

Metabolic Stability

Metabolic stability studies were conducted on Compounds A, A1, and A2 as well as Example 128 of WO 2012/151525 using mouse, rat, dog, monkey, and human liver microsomes. The protocol for the studies with mouse, rat, and human liver microsomes (all from BD Gentest, USA) is provided below. 0.4 mg protein was preincubated with 2 mM NADPH (cofactor) in phosphate buffer (pH ~7.4) for 15 minutes at 37° C. and then added with 1 μM test item and incubated further for 60 minutes in triplicate. The reaction mixture was terminated with methanol containing an internal standard and centrifuged further to analyze the test item remaining in the supernatant by LC-MS/MS. The percent parent compound remaining was calculated in comparison with similar samples terminated at 0 minutes. The results are provided in Table 1 below.

The metabolic stability data for Compound A1 indicates that it exhibits a superior pharmacokinetic profile.

TABLE 1

| Compound | Metabolic stability in liver microsomes | | | | |
|---|---|---|---|---|---|
| | Mouse | Rat | Dog | Monkey | Human |
| Example 128 of WO 2012/151525 | 85.0 | 73.3 | ND | ND | 70.4 |
| Compound A | 96 | 91 | 64.3 | 42.3 | 69.7 |
| Compound A1 | 85.9 | 94.2 | 83.5 | 78.8 | 95.7 |
| Compound A2 | 68.9 | 79.5 | 52.3 | 1.9 | 60.2 |

ND—Not Determined

Protein Binding

Below is provided the procedure for measuring plasma protein binding (using an equilibrium dialysis method). 745 µL of plasma was transferred into a 2 ml micro centrifuge tube. To that 5 µL of Compound A1 (150 µM) was added. Samples were mixed in the table top vortexer for 2 minutes. 50 µL plasma (n=2) was transferred in a pre-labeled 1.5 mL micro centrifuge tube treated as 0 hour sample.

The remaining 650 µL plasma sample were incubated for 30 minutes at 37° C. in a water bath. After 30 minute incubation, 50 µL plasma (n=2) was removed in a pre-labelled 1.5 mL micro centrifuge tube treated as 0.5 hour sample. 200 µL of the plasma sample (n=2) was transferred into the sample chamber which was indicated by the red ring. The red insert was placed into the base plate and 350 µL of buffer was transferred into the buffer chamber. Plates were incubated at 37° C. at approximately 100 RPM on an orbital shaker or 20 RPM on an up-and-down shaker for 4 hours. 50 µL of post dialysis-sample from the buffer and the plasma chambers were transferred into a pre-labelled micro centrifuged tube. 50 µL of plasma was added to the buffer samples and an equal volume of buffer ($KH_2PO_4$ Buffer pH 7.4) to the collected plasma samples. 150 µL of methanol containing internal standard (Tolbutamide 250 ng/ml) was added to precipitate the protein and release compound. Samples were vortexed for 3 minutes in a table top vortexer and centrifuge for 5 minutes at 14,000 RPM. Supernatant was subjected to LC-MS/MS analysis.

The plasma protein binding data for Compound A1 is provided in Table 2 below:

TABLE 2

| Protein Binding (%) | | | | |
|---|---|---|---|---|
| Mouse | Rat | Dog | Monkey | Human |
| 97.61 | 99.04 | 95.85 | 94.71 | 97.24 |

Pharmacokinetics

The oral bioavailability of Compound A1 (free base) was evaluated in rats and mice. The protocol for the pharmacokinetics studies in rat is provided below.

All animals were fasted overnight (12 hours) before dosing and continued till 4.0 hours after administration of test item. Test item formulations were prepared in 1% Tween 80 and 99% media (0.5% Methyl cellulose, 4000 cPs, pH 2.2). The blood samples (150 µL from each animal) were collected from the orbital sinus, and placed into a micro centrifuge tube containing disodium EDTA as an anticoagulant. Blood samples were centrifuged immediately with a speed of 1000 g for 10 min at 4° C. and separated plasma samples were frozen at below −80° C. and stored until analysis. The concentrations of test item in all formulations were analyzed by HPLC. The plasma concentrations of test item in all samples were analyzed by LC-MS/MS. Pharmacokinetic parameters ($C_{max}$, $AUC_{0-t}$, $T_{max}$, and $t_{1/2}$) were estimated by using WinNonlin software. Results are provided in Table 3 for Compound A, A1, and Example 128 of WO 2012/151525 in rats and Compound A1 in mice.

TABLE 3

| Compound | Units | Ex. 128 of WO 2012/151525 | Compound A | Compound A1 | Compound A1 |
|---|---|---|---|---|---|
| Animal | | | Rat | | Mice |
| Route | | Oral | Oral | Oral | Oral |
| Dose | mg/kg | 10 | 10 | 10 | 10 |
| N | | 2 | 2 | 4 | 3 |
| $C_{max}$ | µM | 0.68 | 1.02 | 11.38 | 3.78 |

TABLE 3-continued

| Compound | Units | Ex. 128 of WO 2012/151525 | Compound A | Compound A1 | Compound A1 |
|---|---|---|---|---|---|
| $AUC_{0-t}$ | µM · hr | 2.01 | 7.95 | 97.76 | 7.49 |
| $T_{max}$ | Hr | 0.83 | 2.67 | 1.83 | 0.50 |
| $t_{1/2}$ | Hr | 1.56 | 4.52 | 2.45 | 1.45 |

Compounds A and A1 showed superior pharmacokinetic profiles compared to Example 128 of WO 2012/151525. For instance, Compound A showed a ~1.5 fold increase in $C_{max}$, ~4 fold increase in $AUC_{0-t}$, and ~2.8 fold increase in $t_{1/2}$ as compared to Example 128 of WO 2012/151525. Compound A1 showed a ~16 fold increase in $C_{max}$, 48 fold increase in $AUC_{0-t}$, and ~1.6 fold increase in $t_{1/2}$ as compared to Example 128 of WO 2012/151525.

Biological Assays

The pharmacological properties of the compounds described herein may be confirmed by a number of pharmacological assays, as exemplified below.

Assay 1: Fluorescent Determination of PI3 Kinase Enzyme Activity

Phosphoinositide 3 kinases (PI3K) belong to a class of lipid kinases that play a critical role in the regulation of several key cellular processes. The PI3K are capable of phosphorylating the 3-hydroxy position of phosphoinositols thereby generating second messengers involved in downstream signalling events. The homogenous time resolved fluorescence (HTRF) assay allows detection of 3,4,5-triphosphate (PIP3) formed as a result of phosphorylation of phosphotidylinositol 4,5-biphosphate (PIP2) by PI3K isoforms such as α, β, γ or δ.

PI3K isoform activity for α, β, γ or δ was determined using a PI3K human HTRF™ Assay Kit (Millipore, Billerica, Mass.) with modifications. All incubations were carried out at room temperature. 0.5 µl of 40× inhibitor (in 100% DMSO) or 100% DMSO were added to each well of a 384-well white plate (Greiner Bio-One, Monroe, N.C.) containing 14.5 µl 1× reaction buffer/PIP2 (10 mM $MgCl_2$, 5 mM DTT, 1.38 µM PIP2) mix with or without enzyme, followed by 5 µl/well of 400 µM ATP and incubated for an additional 30 minutes. The reaction was terminated by adding 5 µl/well stop solution (Millipore, Billerica, Mass.). 5 µl of detection mix (Millipore, Billerica, Mass.) was then added to each well and incubated for 6-18 hours in the dark. HRTF ratio was measured on a microplate reader (BMG Labtech., Germany) at an excitation wavelength of 337 nm and emission wavelengths of 665 and 615 nm with an integration time of 400 msec counting delay of 50 msec. The results for Compounds A, A1 and A2 are shown in Table 4 below. Comparative data for Compound A1 and Example 128 of WO2012/151525 are provided in Table 5 below.

TABLE 4

| | $IC_{50}$ (nM) | | | |
|---|---|---|---|---|
| Compound | Pi3Kδ | Pi3Kα | Pi3Kβ | Pi3Kγ |
| A | 102.8 | ND | ND | 82.94 |
| A1 | 30.46 | >10000 | 1359 | 48.72 |
| A2 | 92.95 | ND | ND | >10 µM |

ND: Not Determined

TABLE 5

Selectivity profile

| Compound | IC$_{50}$ (nM) PI3Kδ | IC$_{50}$ (nM) PI3Kγ | Fold-Selectivity PI3Kα | Fold-Selectivity PI3Kβ |
|---|---|---|---|---|
| Example 128 of WO 2012/151525 | 76.01 | 70.70 | NC (38.29*) | NC (51.04*) |
| Compound A | 102.8 | 82.94 | ND | ND |
| Compound A1 | 30.46 | 48.72 | >329 (23.02**) | >45 (46.8*) (IC$_{50}$ = 1359 nM) |
| Compound A2 | 92.95 | >10000 | ND | ND |

\*% inhibition @ 1 μM;
\*\*% inhibition @ 10 uM;
NC—Not Calculated and
ND: Not Determined Assay 2: In Vitro Cell Proliferation Assay in Leukemic Cell Lines Growth inhibition assays were carried out using 10% FBS supplemented media. Cells were seeded at a concentration of 5000-20,000 cells/well in a 96-well plate. Test compounds at a concentration ranging from 0.01 to 10000 nM were added after 24 hours. Growth was assessed using the 3-[4,5-dimethylthiazol-2-yl]-2,5-diphenyltetrazolium bromide (MTT) dye reduction test at 0 hour (prior to the addition of the test compound) and 72 hours after the addition of test compound. Absorbance was read on a Fluostar Optima (BMG Labtech, Germany) at a wavelength of 450 nm. Data were analysed using GraphPad Prism and percent inhibition due to the test compound compared to the control was calculated accordingly.

Compound A1 caused a reduction in T-lymphoma (MOLT-4, Jurkat, CCRF-CEM, Hut-78 and HuT-102) cell viability with GI$_{50}$ values ranging from 2.5-12.8 M for the dose range tested. Additionally, compound A1 did not display any apparent cytotoxicity over the 72 hour incubation period.

Assay 3: Inhibition of AKT Phosphorylation in Leukemic Cell Lines

MOLT-4, Jurkat, CCRF-CEM, and Hut-78 cells were incubated with desired concentrations of compound for 48 hours. Cells were lysed and pAKT determined by Western Blotting. Bands were quantified using ImageJ and normalized to actin.

Compound A1 caused a reduction in pAKT expression in T-lymphoma (MOLT-4, Jurkat, CCRF-CEM and Hut-78) cell lines with EC$_{50}$ values ranging from 0.02-1.6 μM for the dose range tested.

Assay 4: Inhibition of PI3K δ and γ Signalling in Basophils from Human Whole Blood PI3K δ and γ signalling in basophils manifested by an alteration of anti-FcεR1 or fMLP induced CD63 expression is a useful pharmacodynamic marker determined using the Flow2CAST® kit (Buhlmann Laboratories, Switzerland). The test procedure involves the following steps:

- Mix the anti-coagulated blood sample by inverting the venipuncture tube several times;
- Prepare fresh and pyrogen-free 3.5 ml polypropylene or polystyrene tubes suitable for Flow Cytometry measurements;
- Add 49 μl of patient's whole blood to each tube;
- Add 1 μl of 10% DMSO (background) or test compound (10% DMSO) to the assigned tubes and mix gently. Incubate at room temperature for 15 minutes;
- Pipet 50 μl of the Stimulation buffer (background) or anti-FcεRI Ab or fMLP to each tube;
- Add 100 μl of Stimulation Buffer to each tube;
- Mix gently. Add 20 μl Staining Reagent (1:1 mix of FITC-CD63 and PE-CCR3) to each tube;
- Mix gently, cover the tubes and incubate for 15 minutes at 37° C. in a water bath. (using an incubator will take about 10 minutes longer incubation time due to less efficient heat transfer);
- Add 2 ml pre-warmed (18-28° C.) Lysing Reagent to each tube, mix gently;
- Incubate for 5-10 minutes at 18-28° C.;
- Centrifuge the tubes for 5 minutes at 500×g;
- Decant the supernatant by using blotting paper;
- Resuspend the cell pellet with 300-800 μl of Wash Buffer; and
- Vortex gently and acquire the data on the flow cytometer within the same day.

Percent CD63 positive cells within the gated basophil population were determined in different treatment groups and normalized to vehicle control.

Compound A1 exhibited an EC$_{50}$ of <30 nM for FcεR1 (PI3K δ) and an IC$_{50}$ of <70 nM for fMLP (PI3K γ)(n=1).

Assay 4A: Cellular Activity Demonstrating Selectivity of Compound A1 Towards PI3K Delta and PI3K Gamma Isoforms Assay 4A1: Anti-IgM induced B-Cell Proliferation (for PI3Kδ Selectivity)

The objective of this study was to assess the inhibitory potential of Compound A1 on anti-IgM induced human B-cell proliferation.

Plating and Treatment

- Isolated B-cells were re-suspended to 1.0×10$^6$ cells per ml. 100 μl of cell suspension was added to each well of a 96-well plate. Triplicates were maintained.
- 50 μl of drug dilution was added and mixed well. A DMSO blank and inducer blank were maintained.
- The treated plate was incubated for 30 minutes at 37° C., 5% CO$_2$ and then 50 μl of 4× inducer was added and mixed by pipetting.
- The plate was incubated at 37° C., 5% CO$_2$ for 72 hours.
- Media was aspirated and 150 μl of DMSO was added to dissolve the formazan crystals.
- Absorbance was read at A$_{560}$ and A$_{640}$ nm.

The data demonstrates the inhibitory potential of Compound A1 on PI3Kδ mediated induction of human B-cell proliferation. See, e.g., Baeker et al., *Journal of Immunology*, 134: 3532-3538, 1985.

Assay 4A2: LPA Induced AktS473 Phosphorylation in 3T3 Fibroblasts (for PI3Kβ Selectivity)

The objective of this study was to determine the effect of Compound A1 on PI3Kβ kinase mediated LPA induced AktS473 phosphorylation in 3T3 fibroblasts.

- 3T3 cells were treated with desired concentrations of the test compound for 15 minutes. 1 ml of 2×LPA was added such that the final concentration was 5 M and incubated for 5 minutes.
- Media was discarded and washed with 1 ml of ice-cold 1×PBS.
- 250 μl of cell lysis buffer was added and incubated on ice for 30 minutes.
- Samples were centrifuged and supernatant was maintained at −80° C. until analysis.
- Samples were analyzed by Western Blotting using pAKT (S473) as the primary and anti-rabbit IgG-HRP as a secondary antibody.

Intensity of the bands was determined using ImageJ 1.42q (NIH, USA) and normalized to Actin (loading control).

Data was plotted using GraphPad Prism (Version 5.02).

The results demonstrate the selectivity of Compound A1 over the beta isoform of PI3K. See Albuquerque et al., J. Biol. Chem., 278, 39830-39838, 2003.

Assay 4A3: c5a Induced AktS473 Phosphorylation in RAW 264.7 Macrophages (for PI3Kγ Selectivity)

The objective of this study was to determine the effect of Compound A1 on PI3Kγ kinase mediated c5a induced AktS473 phosphorylation in RAW 264.7 macrophages.

RAW 264.7 cells were treated with desired concentrations of the test compound for 15 minutes. 1 ml of 2× c5a was added such that the final concentration was 50 ng/ml and incubated for 15 minutes.

Media was discarded and washed with 1 ml of ice-cold 1×PBS.

250 µl of cell lysis buffer was added and incubated on ice for 30 minutes.

Samples were centrifuged and supernatant was stored at −80° C. until analysis

Samples were analyzed by Western Blotting using pAKT (S473) as the primary and anti-rabbit IgG-HRP as a secondary antibody.

Intensity of the bands was determined using ImageJ 1.42q (NIH, USA) and normalized to Actin (loading control).

Data was plotted using GraphPad Prism (Version 5.02).

Inhibition of pAktS473, a downstream marker of PI3K$_\gamma$ signalling suggests a role for Compound A1 in the oncogenic pathways regulated by Akt in c5a induced RAW 264.7 cells. See To et al., Am. J. Respir. Crit. Care Med., 182, 897-904, 2010.

Assay 4A4: PDGF Induced Akt Phosphorylation in 3T3 Cells (for PI3K α Selectivity)

The objective of this study was to determine the effect of Compound A1 on PI3Kα kinase mediated AktS473 phosphorylation in PDGF induced 3T3 fibroblasts.

3T3 cells were treated with desired concentrations of the test compound for 15 minutes. 1 ml of 2×PDGF was added such that the final concentration was 20 ng/ml and incubated for 10 minutes.

Media was discarded and washed with 1 ml of ice-cold 1×PBS.

250 µl of cell lysis buffer was added and incubated on ice for 30 minutes.

Samples were centrifuged and supernatant was collected and stored at −80° C. until analysis.

Samples were analyzed by Western Blotting using pAKT (S473) as the primary and anti-rabbit IgG-HRP as a secondary antibody.

Intensity of the bands was determined using ImageJ 1.42q (NIH, USA) and normalized to Actin (loading control).

Data was plotted using GraphPad Prism (Version 5.02).

No inhibition was observed at 10 µM of Compound A1, demonstrating the selectivity of Compound A1 over the alpha isoform of PI3K. See Albuquerque et al., J. Biol. Chem. 278, 39830-39838, 2003.

Table 6 below summarizes the results from Assays 4A1-4A4.

TABLE 6

CELLULAR ACTIVITY DEMONSTRATING SELECTIVITY OF COMPOUND A1 TOWARDS PI3K δ AND PI3K γ ISOFORMS

| | |
|---|---|
| Cellular IC$_{50}$ PI3K alpha (PDGF induced pAKT in 3T3 fibroblasts) | >10000 nM |
| Cellular IC$_{50}$ PI3K beta (LPA induced pAKT in 3T3 fibroblasts) | 1324 nM |
| Cellular IC$_{50}$ PI3K delta (anti-IgM induced human B-cell proliferation) | 11.03 nM |
| Cellular IC$_{50}$ PI3K gamma (c5a induced pAKT in RAW macrophages) | 51.73 nM |

Assay 5: Inhibition of Apoptosis in Leukemic Cell Lines

Apoptosis in leukemic cells was determined using an in situ Caspase 3 kit (Millipore, US) as outlined below:

Seed leukemic cells at a density of 1×10$^6$ cells/well in a 6 well plate

Add test compound/DMSO at desired concentrations

Incubate the plate for 24 hours at 37° C. in 5% CO$_2$ incubator

Collect cells in a 2 ml centrifuge tube

Add 1.6 µL of freshly prepared 5×FLICA reagent and mix cells by slightly flicking the tubes Incubate tubes for 1 hour at 37° C. under 5% CO$_2$ Add 2 ml of 1× wash buffer to each tube and mix Centrifuge cells at <400×g for 5 minutes at room temperature.

Carefully remove and discard supernatant, and gently vortex cell pellet to disrupt any cell-to-cell clumping.

Re-suspend cell pellet in 300 ul of 1× wash buffer

Place 100 µL of each cell suspension into each of two wells of a black microtiter plate. Avoid creation of bubbles.

Read absorbance of each microwell using an excitation wavelength of 490 nm and an emission wavelength of 520 nm.

Percent increase in caspase-3 activity manifested by an increase in fluorescence compared to the control blank is to be calculated.

Assay 6A: Cytokine Assay in Human PBMC

The objective of this study was to assess the inhibitory potential of Compound A1 on antigen-induced cytokine release in human PBMC Plating and Treatment Heparinized human whole blood was diluted 1:1 with PBS, over laid on leukocyte separation medium and centrifuged at 400 g for 40 minutes.

Buffy layer was removed and washed with PBS 0.15*10$^6$ of PBMCs were plated in 100 µl per well in RPMI media and incubated for 2 h.

50 µl of 3× of the compound dilution in media was added and incubated for 15 min.

TNFα—induced with 50 µl of LPS in RPMI such that final concentration was 1 µg/ml. Supernatant was collected at 6 hours.

IL-2—induced with 50 µl of PHA in RPMI such that final concentration was 20 µg/ml. Supernatant was collected at 24 hours.

IL-4—induced with 50 µl of PHA in RPMI such that final concentration was 20 µg/ml. Supernatant was collected at 48 hours.

ELISA was performed used kits from eBioscience.

EC$_{50}$ was calculated using GraphPad Prism 5.

EC$_{50}$ values were calculated from 2-3 independent experiments. Compound A1 inhibited antigen-induced TNFα, IL-2, and IL-4 with an EC$_{50}$ of 7.1, 9.5, and 3.5 nM, respectively.

Assay 6B: Inhibition of LPS Induced CD19 or CD45R in Human or Mouse Whole Blood

The effect of Compound A1 on modulating B-cell receptor (BCR)-activated proliferation of human or mouse B-lymphocytes was determined. CD19 is a protein present on B cells from the earliest recognizable B-lineage cells during development to B-cell blasts but is however lost on maturation to plasma cells. LPS is an endotoxin and a major component of environmental microbes with a potent mitogenic activity on B-cells via the BCR signaling pathway.

Diluted human whole blood was treated with DMSO or desired concentrations of Compound A1. Samples were induced with LPS 15 minutes after addition of compound and incubated for 72 hours at 37° C. and 5% $CO_2$. Cells positive for CD45 and CD19 were determined by flow cytometry and data are expressed as percentage CD19 positive cells in the total population. Treatment with Compound A1 resulted in a dose-dependent inhibition of LPS-induced human whole blood B-cell proliferation ($EC_{50}$=117.7 nM) manifested by a reduction in CD19 expression.

Similar to CD19, CD45R (B220) is expressed on mouse B-lymphocytes throughout their development from early pro-B stages onwards and is down-regulated upon terminal differentiation to plasma cells. Briefly, diluted mouse whole blood was treated with of DMSO or desired concentrations of Compound A1. Samples were induced with LPS 15 minutes after compound addition, and incubated for 72 hours at 37° C. and 5% $CO_2$. Cells positive for CD45 and CD45R were determined by flow cytometry. Data are expressed as percentage CD45R positive cells in the total population. Consistent with CD19+ cell proliferation data, treatment with Compound A1 resulted in a dose-dependent inhibition of LPS-induced mouse whole blood B-cell proliferation ($EC_{50}$=128.2 nM) manifested by a reduction in CD45R expression.

Assay 6C: Inhibition of AKT Phosphorylation in Isolated Mouse Splenocytes

The PI3K pathway is regulated downstream by AKT, a serine-threonine kinase that modulates several oncogenic processes such as cell proliferation, growth, and survival. Because the spleen is a repertoire for vast quantities of B- and T-lymphocytes, inhibition of LPS-induced AKT phosphorylation was determined ex vivo using isolated mouse splenocytes. Cells were plated and incubated with a desired concentration of Compound A1 for 15 minutes followed by induction with LPS (20 g/mL) for 30 minutes. Following induction, cells were lysed and pAKT was determined by ELISA using $pAKTS^{473}$ capture/detection antibody pair and anti-mouse-HRP secondary antibody. Blank subtracted absorbance values were obtained to calculate percent inhibition of pAKT in test samples. Compound A1 caused a dose-dependent reduction ($EC_{50}$=347.4 nM) in phosphorylation of the downstream marker, AKT, at low concentrations thereby elucidating the signaling pathway Assay 7: Lipopolysaccharide Induced Pulmonary Neutrophilia in Female Wistar Rat Model An exaggerated recruitment and subsequent activation of neutrophil is likely to be important for the development and course of several inflammatory diseases in the airways and lungs, such as severe asthma, chronic obstructive pulmonary disease, cystic fibrosis, and acute respiratory distress syndrome. The mechanisms by which neutrophil contributes to these diseases may involve the release of proteolytic enzymes, such as neutrophil elastase, and free oxygen radicals. When released, these compounds can cause bronchoconstriction, bronchial hyperreactivity, hyper-secretion, epithelial damage, and tissue remodelling in the airways.

After the quarantine period, fasted animals were randomized and divided into various groups depending on their body weights. The test compound (Compound A1) was prepared as a suspension in a vehicle consisting of 0.5% methylcellulose in which Tween 80 as a suspending agent. The compound or vehicle was administered by oral gavage at a volume of 10 mL/kg. Female Wistar rats were anaesthetized with ketamine and LPS solution was administered intratracheally one hour after compound administration at a dose of 1 mg/kg. 6 hours after LPS instillation, animals were exsanguinated under anaesthesia, and then the trachea was cannulated and the lungs were lavaged with 5 ml aliquots of heparinised PBS (1 unit/ml) four times through a tracheal cannula (total volume 20 mL). Bronchoalveolar lavage (BAL) fluid was stored at 2-8° C. until assayed for total cell and differential leukocyte count. Bronchioalveolar fluid was centrifuged (500×g for 10 minutes) and the resulting cell pellet was resuspended in 0.5 ml of heparinised saline. The total numbers of white blood cells were determined in BAL fluid or blood by using a blood cell counter and was adjusted to $1 \times 10^6$ cell/ml. Differential cell count was calculated manually. One hundred microliters of the cell suspension was centrifuged using a Cytospin 3 to prepare a cell smear. The cell smear was stained with a blood staining solution for differentiation and slides were microscopically observed to identify eosinophil according to their morphological characteristics. The number of each cell type among 300 white blood cells in the cell smear was determined and expressed as a percentage. The number of eosinophil in each BALf or blood was calculated.

Compound A1 showed a reduction of neutrophil infiltration into the lungs with an inhibition of 65.29% at 10 mg/kg compared to the control group, suggesting a therapeutic role in inflammatory disorders. The results are shown in FIG. 1.

Assay 8: Lipopolysaccharide-Induced Rat Air Pouch Model of Inflammation

Female Wistar rats (175-200 g) were acclimatized for seven days prior to the start of the experiment. Animals were randomly distributed to various groups based on their body weights. Animals were anaesthetised with ether and subcutaneous air pouches were made by injecting 20 ml of sterile air under the skin in the intra-scapular area (day 0) and maintained with a second 10 ml injection of sterile-filtered air on day 4. On day 6, oral treatment was commenced 1 hour prior to induction of inflammation by s.c. injection of LPS solution on day 6. A volume of 5 ml of LPS solution dissolved in sterile saline (100 μg/kg) was injected into each pouch. Samples of pouch fluid were taken at 6 h after administration of LPS by flushing the pouch with 5 ml of sterile saline and withdrawing 4 ml of fluid. The number of leukocytes present in pouch fluid was determined microscopically using a haemocytometer. Differential cell content was determined by microscopic examination of fluid smears stained with Diff-Quik.

Figure 2:
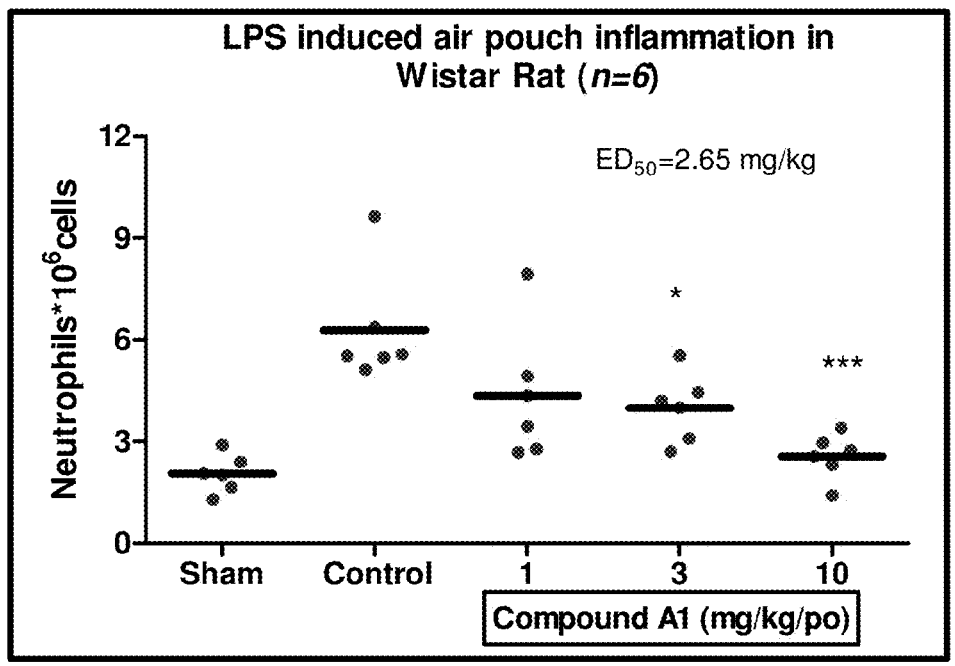
FIG. 2 depicts a bar graph of the neutrophil count in peritoneal lavage fluid from Wistar rats treated with 1, 3, and 10 mg/kg of Compound A1 (po) according to the lipopolysaccharide-induced rat air pouch inflammation model described in Assay 8.

Compound A1 caused a dose-dependent reduction of neutrophil migration into the rat air pouch with an $ED_{50}$ of 2.65 mg/kg suggesting a therapeutic role in rheumatoid arthritis. The results are shown in FIG. 2.

Assay 9: Ovalbumin Induced Pulmonary Eosinophilia in Male Guinea Pigs

After the quarantine period, 0.3 ml of blood samples are collected from orbital vein by retro-orbital plexus method from each individual animal and analysed on a cell analyser (ADVIA 2120, Siemens). Based on their total cell count, guinea pigs are randomized and divided into various groups. Ear pinna is marked with an indelible marking pen for identification. On day 0, weights are recorded and animals are sensitized with 50 μg of ovalbumin (OVA) and 10 mg of alum solution (1 ml) intraperitoneally. On day 7 and day 14, the above sensitization protocol is repeated. Animals are observed for any signs of illness or reaction to the sensitization up to day 19 and recorded if any. On day 19, 20, and 21, after the treatment with test compound by oral gavage, 30 minutes later animals are exposed to 0.5% w/v, 0.5% and 1% ovalbumin challenge respectively. Control and sham group animals are treated with 0.5% w/v methyl cellulose (vehicle). Sham control groups are sensitized with 10 mg of alum on day 0, 7 and 14 and exposed to saline solution (SAL) with the same nebulization rate on day 19, 20 and 21. Twenty hours after the last OVA challenge, airway hyper-responsiveness is measured by whole body plethysmograph against cumulative doses of methacholine challenge (75, 100, 125 and 150 µg/ml). After measuring the airway response, blood samples and BAL fluid are collected. Samples are analysed for total cell count by using a neubuear chamber under microscope and differential leukocyte count is done manually.

Assay 10: Murine Asthma Model

After the quarantine period, based on their body weights, mice were randomized and divided into four groups (n=7). Tails were marked with an indelible marking pen for identification. On day 0, weights were recorded and animals were sensitized with 100 µg of ovalbumin and 10 mg of alum solution (0.2 mL) intraperitoneally.

On day 7 and day 14, the above sensitization protocol was repeated. Animals were observed for any signs of illness or reaction to the sensitization up to day 24 and recorded if any. On day 24, 25, and 26, after the treatment with test compound by oral gavage, 30 minutes later animals were exposed to 10% w/v ovalbumin challenge.

Control and sham group animals were treated with 0.5% w/v methyl cellulose (vehicle). Sham control groups were sensitized with 10 mg of alum on day 0, 7 and 14 and exposed to saline solution with the same nebulization rate on day 24, 25 and 26.

Forty eight hours after the last OVA challenge, airway hyperresponsiveness was measured by whole body plethysmograph against cumulative doses of methacholine challenge (2.5, 10, 50 and 100 mg/ml). After measuring the airway response, blood samples and BAL fluid were collected. Samples were analysed for total cell count by using a neubuear chamber under microscope and differential leukocyte count was done manually.

Assay 11: Collagen Induced Arthritis (CIA) in Wistar Rats

Female wistar rats were acclimatized for seven days prior to the start of the experiment and were randomly distributed to various groups based on their body weights. On day 0, animals were treated by intradermal injection of 500 µg of bovine collagen type II emulsified with complete Freund's adjuvant (IFA) containing MTB (4 mg/mL) delivered at the base of the tail. On day 7 after primary immunization, animals were treated by booster injection of 300 µg CII in incomplete Freund's adjuvant by intradermal injection at the base of the tail. Onset of arthritis in ankle joints usually became visually apparent between days 12 and 14. Animals were treated with test compound or vehicle (orally administered) from the day after onset of arthritis and the treatment continued for the next 9 consecutive days. Arthritis Scores were taken by visual examination for signs of joint inflammation regularly throughout the study period. Measurements of body weights, paw volumes, and paw thickness were taken on days 0, 1, 3, 5, 7, 9, and 10. After the ten day treatment, at the end of the study, blood was withdrawn at necropsy and processed to serum or plasma and all joints were taken and both fore paw and hind paws were fixed in 10% formalin for histopathology analysis after taking a small piece of tissue from each joint and stored at −80° C. for cytokine analysis in tissue homogenate. Clinical Scoring Criteria for Fore and Hind Paws: 0=normal; 1=one hind or fore paw joint affected or minimal diffuse erythema and swelling; 2=two hind or fore paw joints affected or mild diffuse erythema and swelling; 3=three hind or fore paw joints affected or moderate diffuse erythema and swelling; 4=marked diffuse erythema and swelling, or =four digit joints affected; 5=severe diffuse erythema and severe swelling entire paw, unable to flex digits.

Figure 3A:
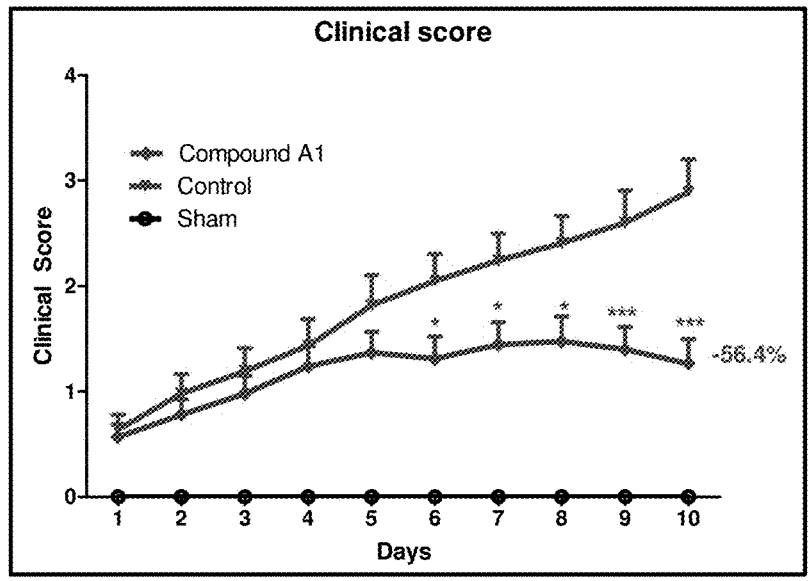
FIGS. 3A and 3B depict the line and bar graphs of individual clinical scores for hind and fore paws and AUC for clinical score, respectively, in Wistar rats with collagen induced arthritis treated with a control or 10 mg/kg/QD of Compound A1 according to the procedure in Assay 11.
Figure 3B:
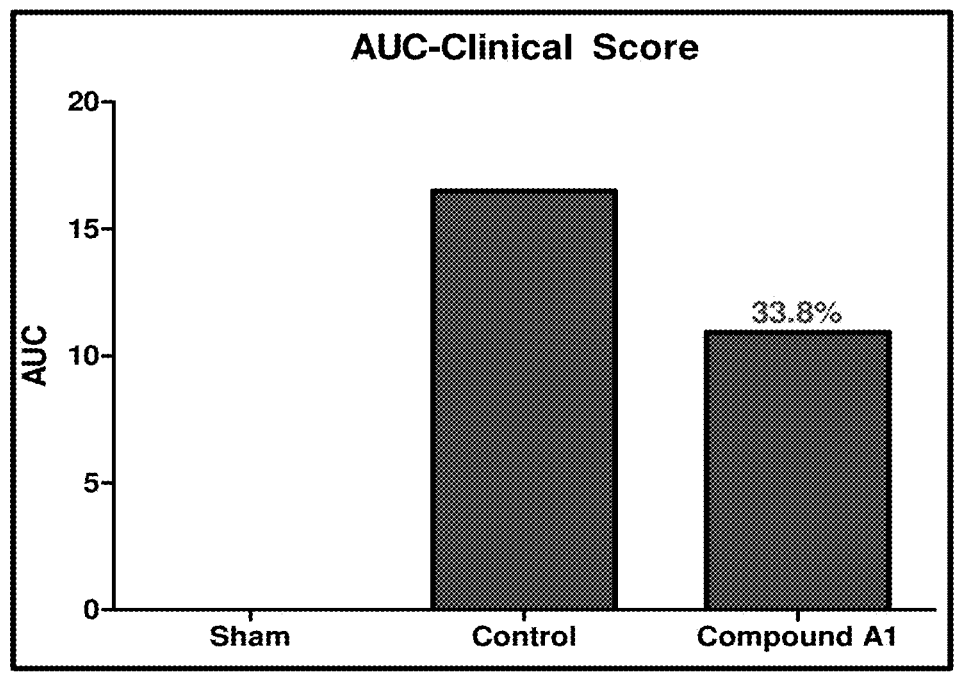
Figure 3C:
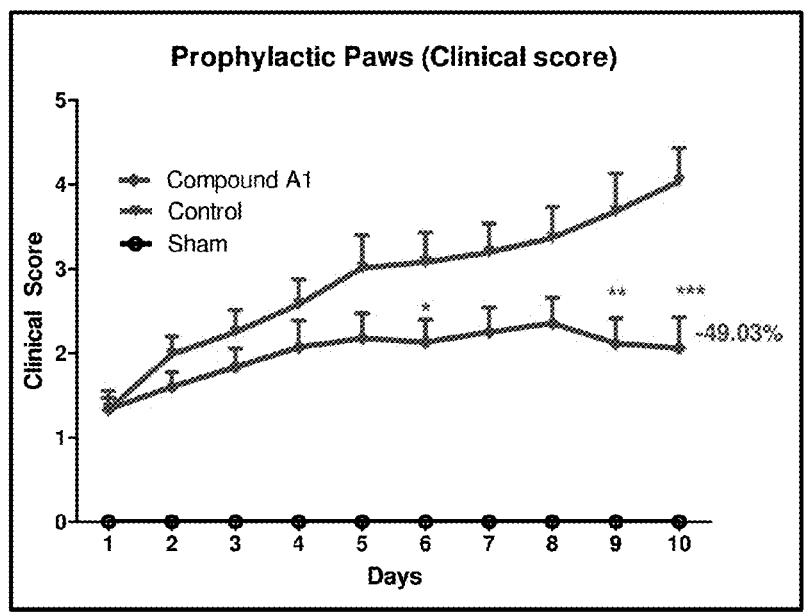
FIGS. 3C and 3D depict line and bar graphs of individual clinical scores for hind and fore paws, respectively, in Wistar rats with collagen induced arthritis treated with vehicle or 10 mg/kg/QD of Compound A1 according to the procedure in Assay 11.
Figure 3D:
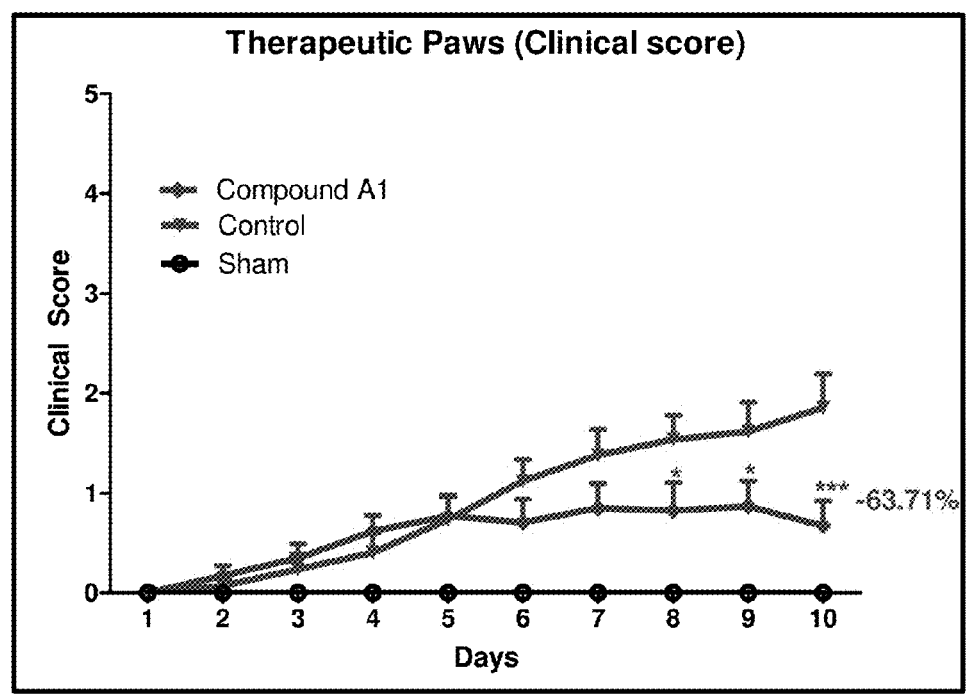

Compound A1 dosed therapeutically in the rat CIA model demonstrates significant efficacy in the reduction of the clinical score (FIGS. 3A and 3B) observed in both prophylactic paws (FIG. 3C) and therapeutic paws (FIG. 3D).

Figure 4A:
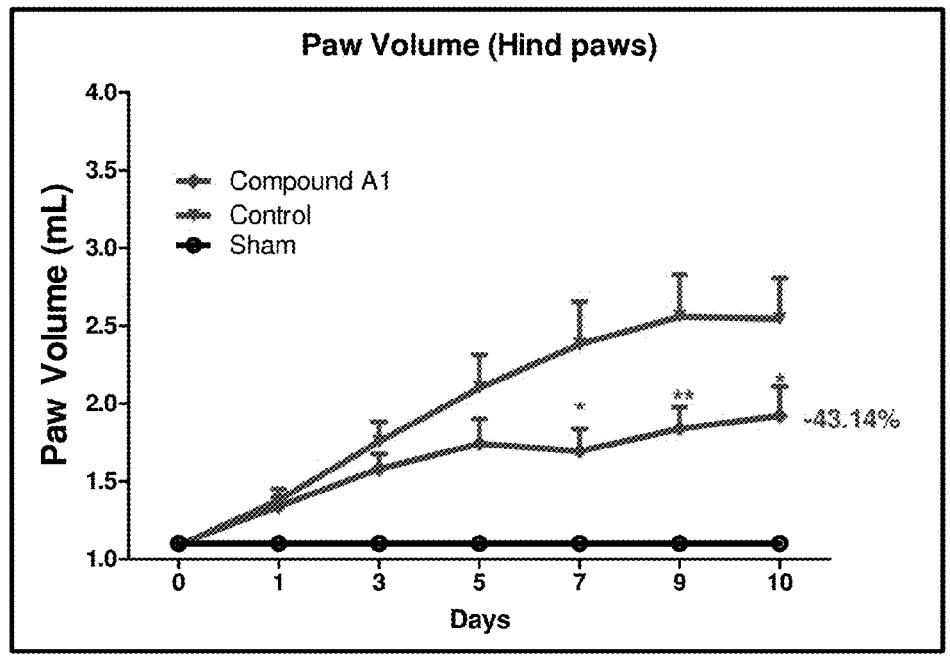
FIGS. 4A and 4B depict the line and bar graphs of volume for hind paws and AUC of paw volume, respectively, in Wistar rats with collagen induced arthritis treated with vehicle or 10 mg/kg/QD of Compound A1 according to the procedure in Assay 11.
Figure 4B:
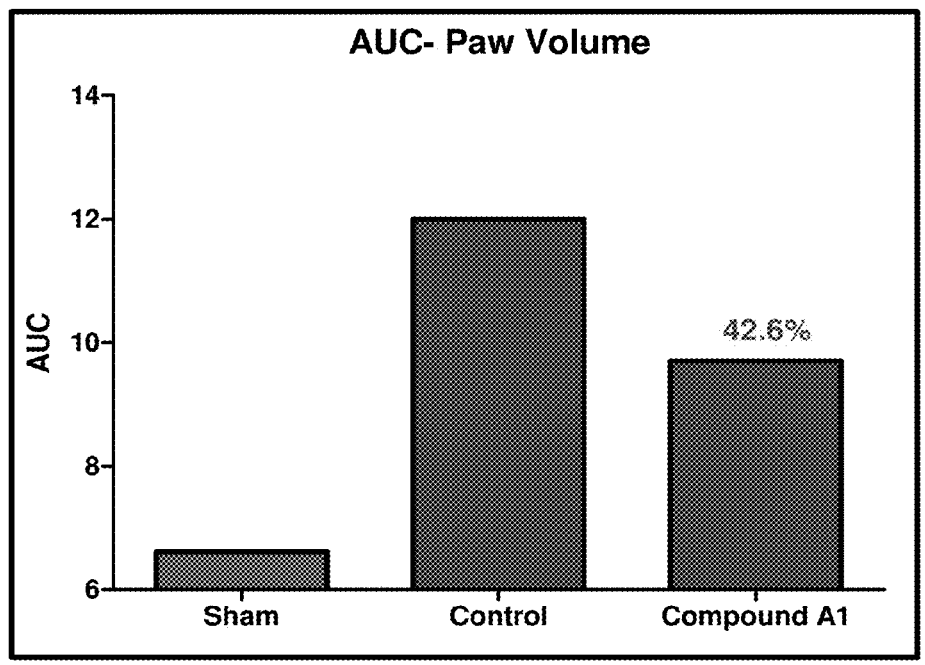
Figure 4C:
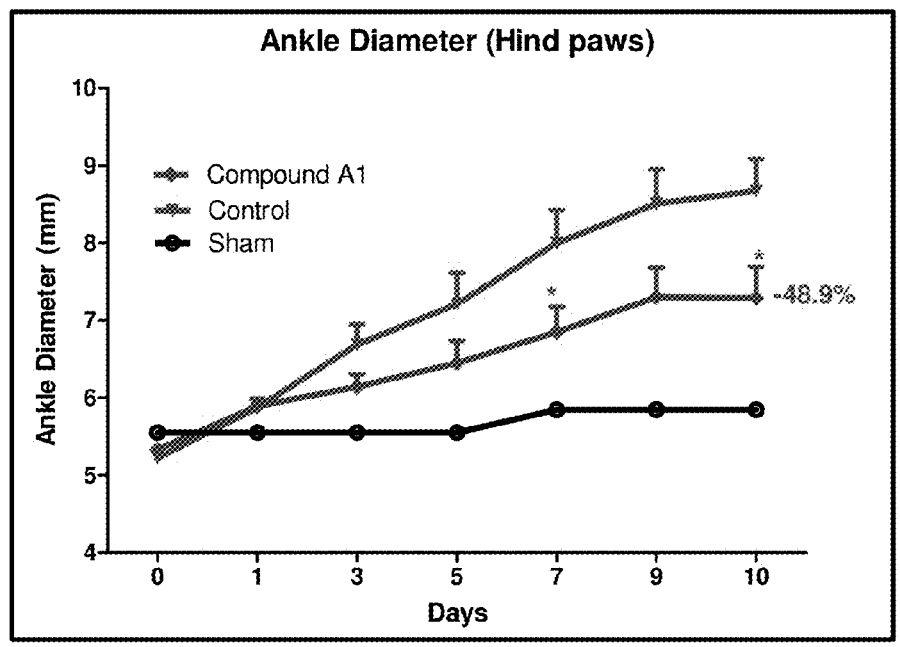
FIGS. 4C and 4D depict line and bar graphs of ankle diameter for hind paws and AUC of ankle diameter, respectively, in Wistar rats with collagen induced arthritis treated with vehicle or 10 mg/kg/QD of Compound A1 according to the procedure in Assay 11.
Figure 4D:
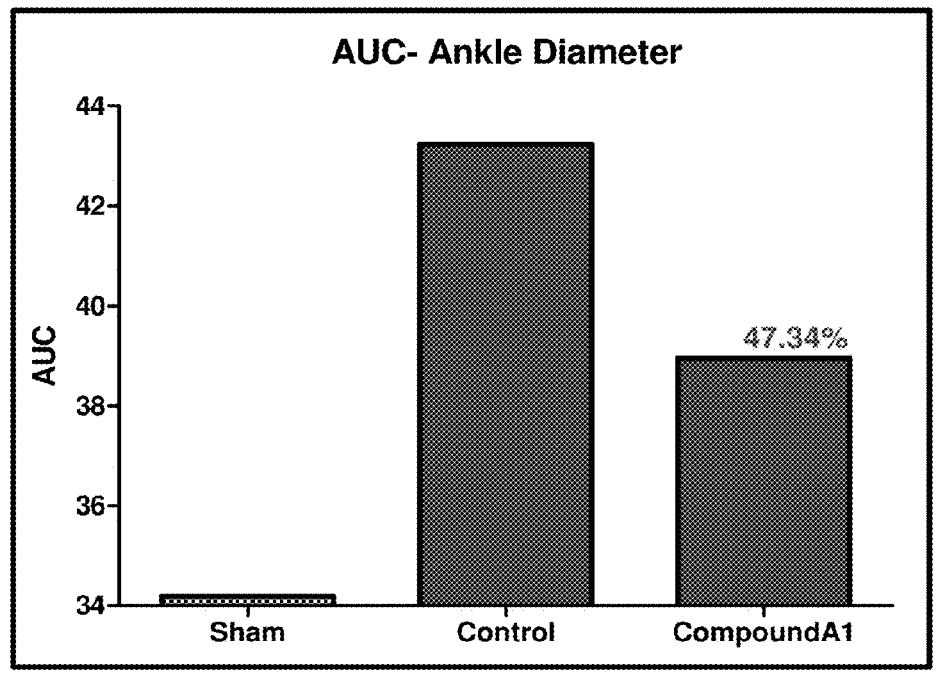
Figure 4E:
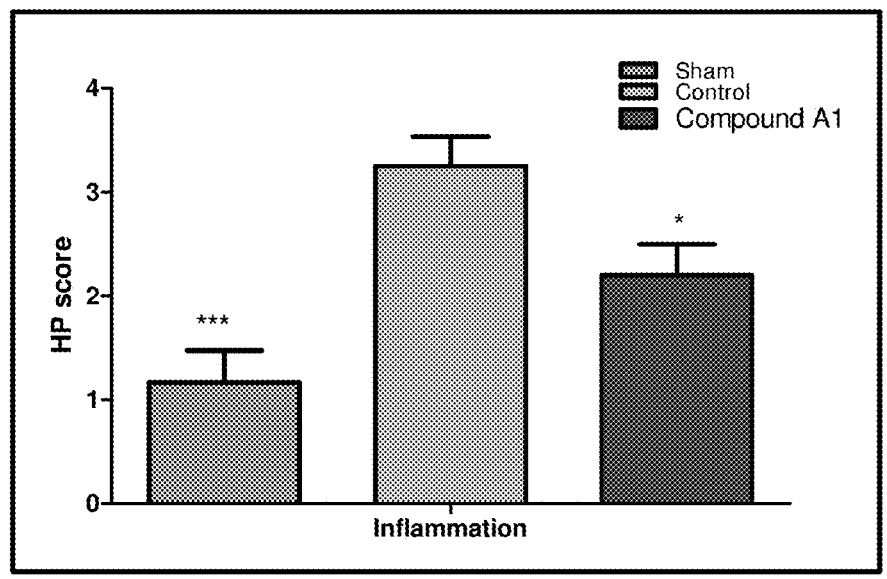
FIGS. 4E to 4G depict bar graphs of histopathological score for inhibition of inflammation, cartilage and pannus, respectively, of all the hind and fore paws in Wistar rats with collagen induced arthritis treated with vehicle or 10 mg/kg/QD of Compound A1 according to the procedure in Assay 11.
Figure 4F:
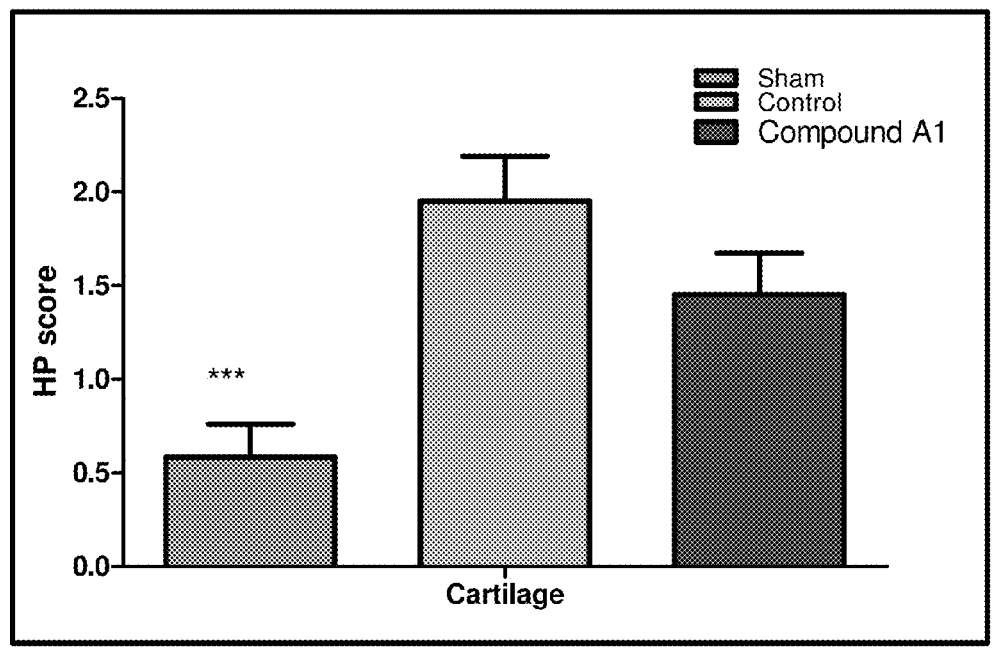
Figure 4G:
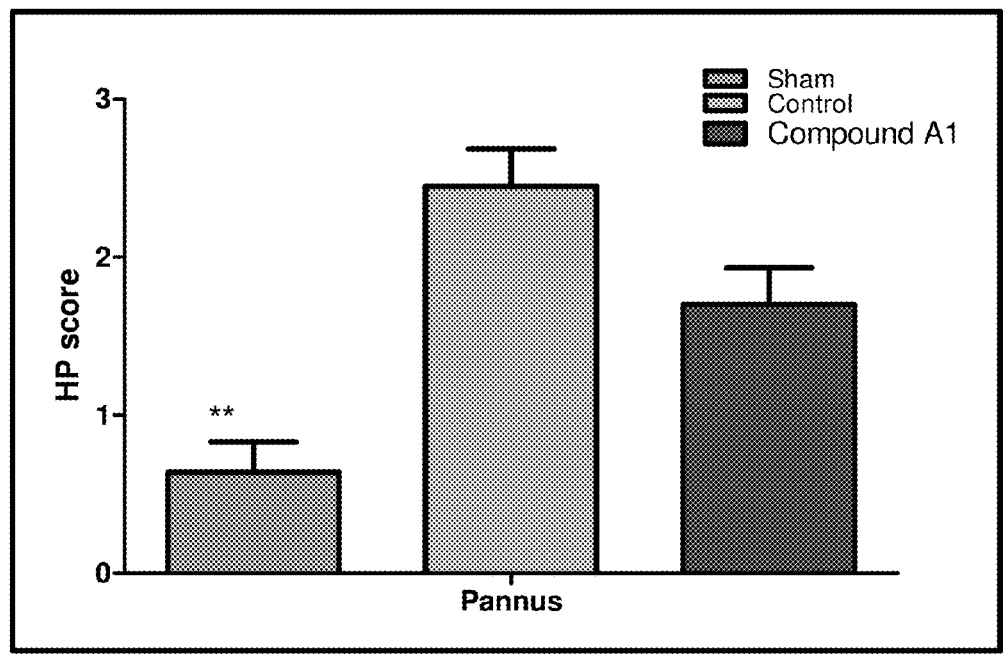
Figure 4H:
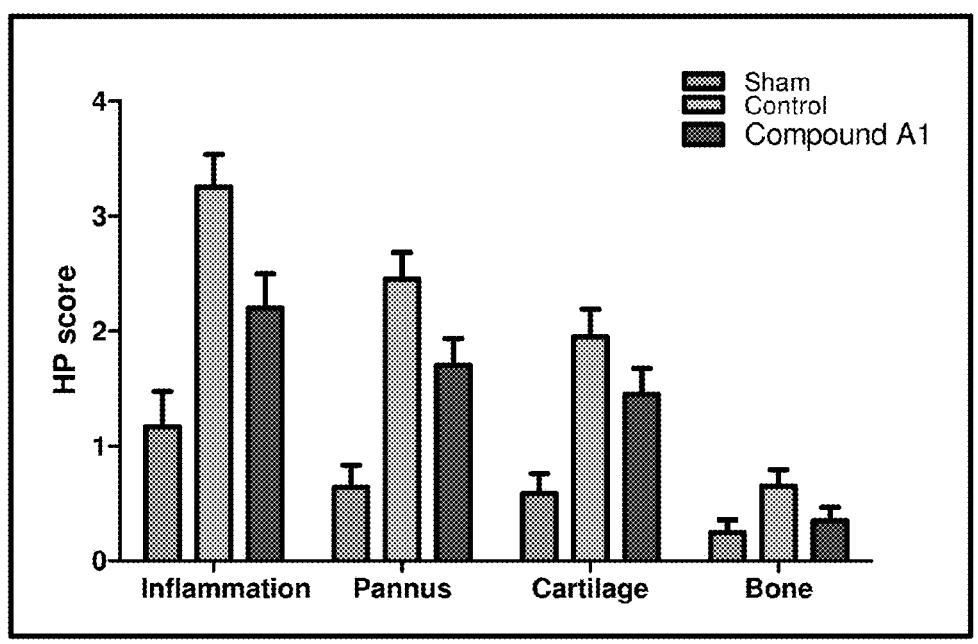
FIG. 4H depicts a bar graph of total histopathological score of all the hind and fore paws in Wistar rats with collagen induced arthritis treated with vehicle or 10 mg/kg/QD of Compound A1 according to the procedure in Assay 11.

Compound A1 dosed therapeutically in the rat CIA model demonstrates significant efficacy in reducing the average paw volumes of both the hind paws (FIGS. 4A and 4B) and in ankle diameter (FIGS. 4C and 4D).

Histological analysis: Compound A1 dosed therapeutically in the rat CIA model demonstrates significant efficacy in inhibition of inflammation (58.3%, see FIG. 4A), cartilage (46.51%, see FIG. 4B) and pannus (49.18%, see FIG. 4C) observed by histopathology of all the hind and fore paws.

Figure 5:
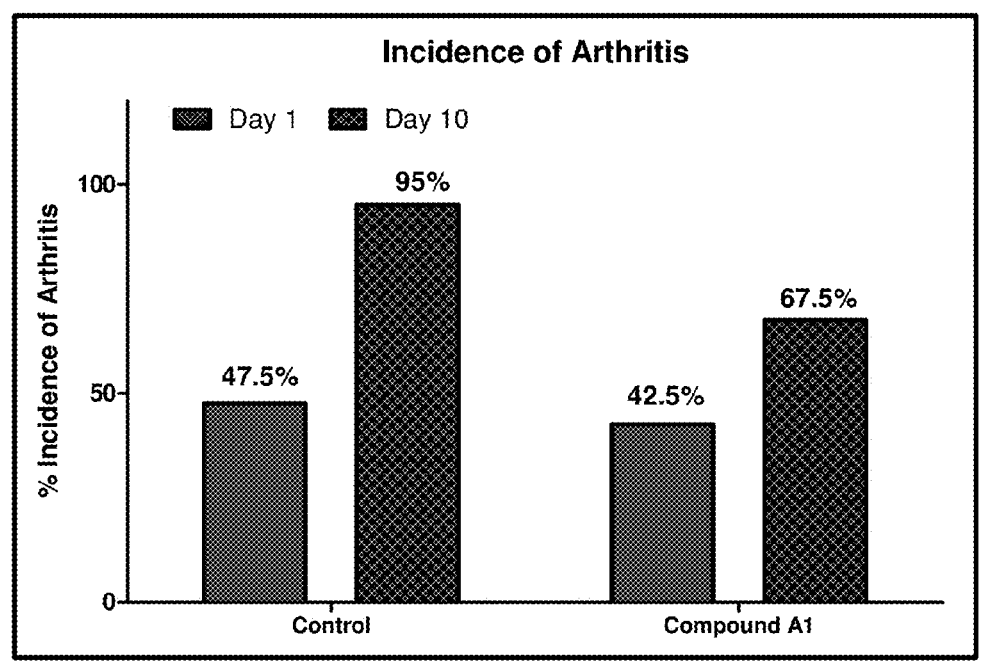
FIG. 5 depicts a bar graph of the percentage incidence of arthritis in Wistar rats with collagen induced arthritis treated with vehicle or 10 mg/kg/QD of Compound A1 according to the procedure in Assay 11.

The incidence and progression of arthritis was significantly reduced in treatment group compared to control group animals (FIG. 5).

Assay 12: Acute Cigarette Smoke Induced Cell Infiltration in Male Balb/c Mice

Animals (male Balb/c mice) are to be acclimatized for seven days prior to the start of the experiment. Animals are then to be randomly distributed to various groups based on their body weights. On day 1, the mice are to be administered test compound or vehicle by oral/intranasal route and after 1 hour, the test compound administered animals are to be placed in a whole body exposure box. On day 1 and day 2, mice are exposed to the mainstream smoke of 6 cigarettes, of 8 cigarettes on day 3, and of 10 cigarettes on day 4. Exposure to the smoke of each cigarette will last for 10 minutes. The cigarettes are to be completely burned in the first two minutes, followed by an air flow with animal ventilator and the next 20 minutes will be exposure with fresh room air. After every second cigarette, an additional break of 20 minutes with exposure to fresh room air is to be conducted. Control animals are to be exposed to room air chamber. From day 1 to day 4, animals will be administered the test compound either by oral or intranasal route. On day 5, 24 hours after the last cigarate smoke (CS) exposure, animals will be exsanguinated under anaesthesia, and the trachea will be cannulated and the lungs lavaged with 0.5-ml aliquots of heparinised PBS (1 unit/ml) four times through tracheal cannula (total volume 2 ml). Bronchioalveolar (BAL) collected is to be stored at 2-8 OC until assayed for total cell and differential leukocyte count. BAL fluid is to be centrifuged (500×g for 10 min) and the resulting cell pellet is resuspended in 0.5 ml of heparinised saline. The total number of white blood cells is to be determined in BAL fluid and blood using a blood cell counter and adjusted to $1 \times 10^6$ cell/ml. Differential cell count is calculated manually. Forty microliters of the cell suspension is centrifuged using Cytospin 3 to prepare a cell smear. The cell smear is stained with a blood staining solution for differentiation and microscopically observed to identify eosinophil according to their morphological characteristics. The number of each cell type among 300 white blood cells in the cell smear are to be determined and expressed as a percentage, and the number of neutrophils and macrophages in each BAL fluid are to be calculated.

Assay 13: Imiquimod Induced Plaque Psoriasis in Balb/c Mice Model

Imiquimod (IMQ) is a ligand for TLR7 and TLR8, originally used for the treatment of non-melanoma skin cancers. The topical application of IMQ on the shaved back skin of the mouse induces a psoriasis-like skin condition exhibiting most of the human psoriasis pathology characteristic features including acanthosis, parakeratosis, and infiltration of immune cells and involvement of the IL23/

IL17/IL22 pathway. Animals (male Balb/c mice) were acclimatized for seven days prior to the start of the experiment. Animals were randomly distributed to various groups based on their body weights. On day 0, the back skin of the mice was shaved by topical application of hair removal cream. On day 1, mice were administered the test compound or vehicle by the oral route and after 1 hour the mice that received the test compound received a topical application of 62.5 mg of commercially available IMQ cream (5%; Beselna Cream; Mochida Pharmaceuticals, Tokyo, Japan) on the shaved back skin. The mice were treated with topical application of imiquimod for the next 5 consecutive days, one hour after test compound or vehicle administration. Animals were allowed to dry for one hour before returning to their cages after topical application on every day. Four hours after the final application of IMQ cream, the mice were killed and skin samples were obtained. Back skin thickness was measured using dial thickness gauge. After measuring skin thickness, skin samples were fixed in 10% neutral buffered formalin solution and embedded in paraffin. Deparaffinised sections were stained with hematoxylin-eosin (HE). Epidermal thickness was quantified by averaging the values of five independent fields per section. To score the severity of inflammation of the back skin, an objective scoring system was used based on the human clinical Psoriasis Area and Severity Index (PASI). Erythema, scaling, and thickening were scored independently on a scale from 0 to 4: 0=none; 1=slight; 2=moderate; 3=marked; and 4=very marked.

Figure 6A:
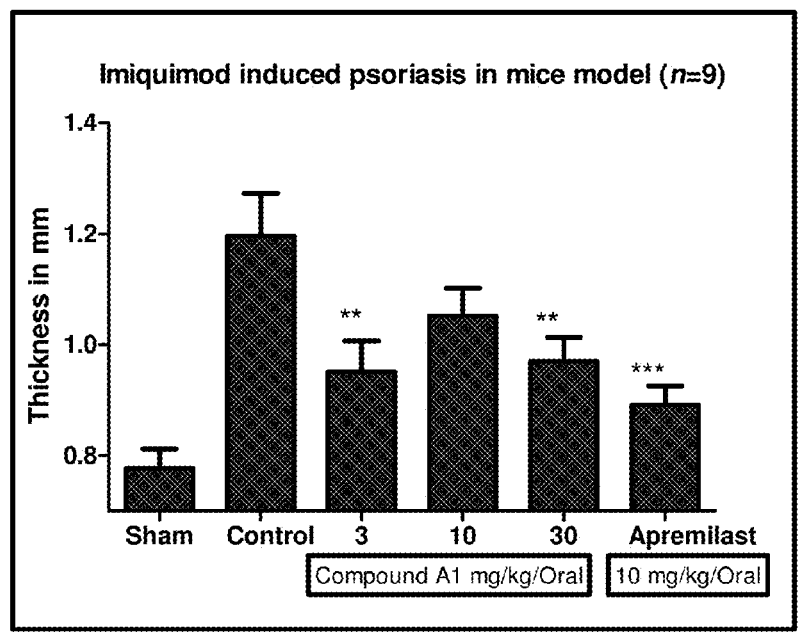
FIGS. 6A and 6B depict bar graphs showing the antipsoratic effect of Compound A1 (3, 10, 30 mg/kg) on imiquimod induced psoriasis in Balb/c mice according to the procedure in Assay 13.
Figure 6B:
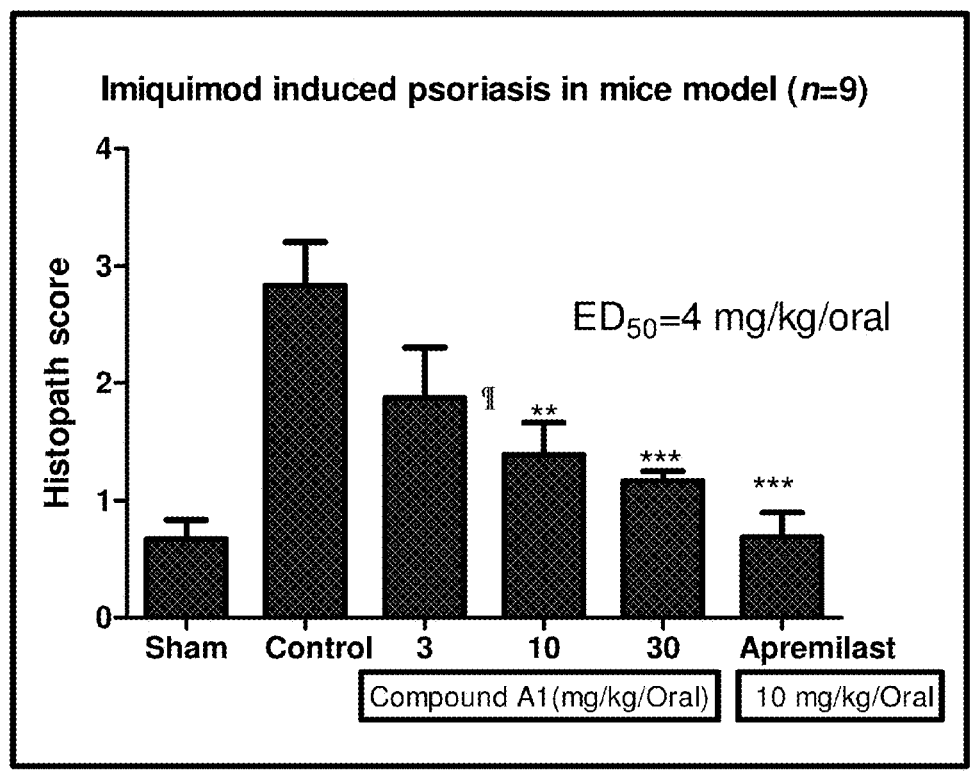

As shown in FIGS. 6A and 6B, Compound A1 reduced back skin thickness, erythema, and scaling (as shown by the histopathological score) compared to the control group animals.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications and patent and/or patent applications cited in this application are herein incorporated by reference to the same extent as if each individual publication or patent application was specifically and individually indicated to be incorporated herein by reference.

What is claimed is:

1. A compound selected from (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide and pharmaceutically acceptable salts thereof.

2. The compound according to claim 1, wherein the compound is substantially free of (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide and pharmaceutically acceptable salt thereof.

3. The compound of claim 1, wherein the compound has an enantiomeric excess greater than about 95%.

4. (S)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide.

5. The compound of claim 4, wherein the compound is substantially free of (R)—N-(5-(4-amino-1-(1-(5-fluoro-3-(3-fluorophenyl)-4-oxo-4H-chromen-2-yl)ethyl)-1H-pyrazolo[3,4-d]pyrimidin-3-yl)-2-methoxyphenyl)methanesulfonamide.

6. The compound of claim 4, wherein the compound has an enantiomeric excess greater than about 95%.

7. A pharmaceutical composition comprising a compound according to claim 1 and at least one pharmaceutically acceptable carrier.

8. A method of treating asthma or chronic obstructive pulmonary disease in a patient in need thereof, the method comprising administering to the patient an effective amount of a compound of claim 1.

9. A method of treating rheumatoid arthritis, psoriasis, lupus or experimental autoimmune encephalomyelitis (EAE) in a patient in need thereof, the method comprising administering to the patient an effective amount of a compound of claim 1.

10. A process for the preparation of compound of formula (A1)

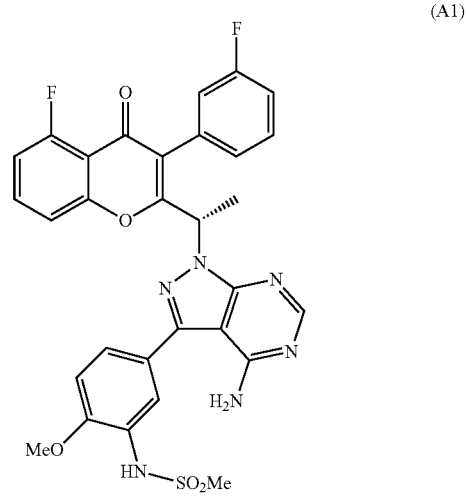 [SMILES: COc1ccc(-c2nn([C@@H](C)c3oc4cccc(F)c4c(=O)c3-c3cccc(F)c3)c3ncnc(N)c23)cc1NS(C)(=O)=O]

comprising the steps of:
(a) reacting (R)-5-fluoro-3-(3-fluorophenyl)-2-(1-hydroxyethyl)-4H-chromen-4-one

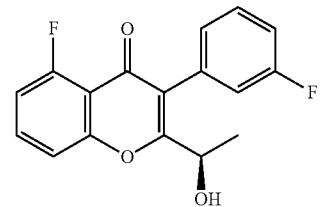 [SMILES: C[C@@H](O)c1oc2cccc(F)c2c(=O)c1-c1cccc(F)c1]

with 3-(4-methoxy-3-nitrophenyl)-1H-pyrazolo[3,4-d]pyrimidin-4-amine

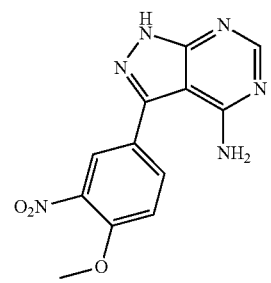 [SMILES: COc1ccc(-c2n[nH]c3ncnc(N)c23)cc1[N+](=O)[O-]]

under Mitsunobu conditions using triphenylphosphine and diisopropylazodicarboxylate to give (S)-2-(1-(4-amino-3-(4-methoxy-3-nitrophenyl)-1H-pyrazolo[3,4-d]pyrimidin-1-yl)ethyl)-5-fluoro-3-(3-fluorophenyl)-4H-chromen-4-one (Intermediate 3)

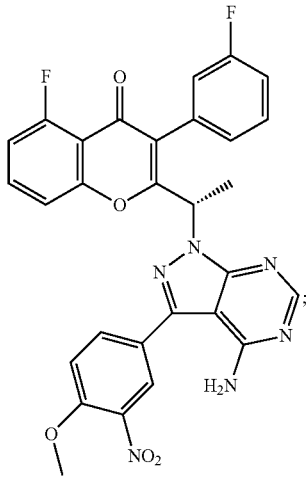

Intermediate 3

(b) reducing intermediate 3 to give (S)-2-(1-(4-amino-3-(3-amino-4-methoxyphenyl)-1H-pyrazolo[3,4-d]pyrimidin-1-yl)ethyl)-5-fluoro-3-(3-fluorophenyl)-4H-chromen-4-one (Intermediate 4)

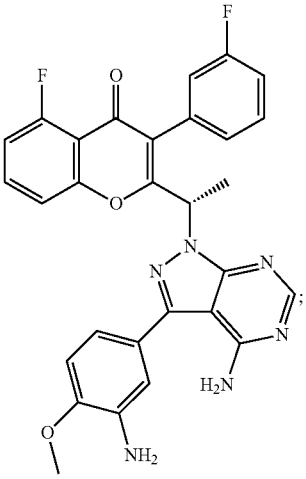

Intermediate 4 and (c) reacting Intermediate 4 with methanesulphonyl chloride to give a compound of the formula (A1).

* * * * *